US012667256B2

(12) United States Patent
Mansouri et al.

(10) Patent No.: US 12,667,256 B2
(45) Date of Patent: *Jun. 30, 2026

(54) EYE EXAMINATION APPARATUS FOR USE WITH A SMARTPHONE

(71) Applicant: Neuroptek Corporation Inc., Winnipeg (CA)

(72) Inventors: Behzad Mansouri, Winnipeg (CA); Neda Anssari, Winnipeg (CA)

(73) Assignee: Neuroptek Corporation Inc. (CA)

( * ) Notice: Subject to any disclaimer, the term of this patent is extended or adjusted under 35 U.S.C. 154(b) by 428 days.

This patent is subject to a terminal disclaimer.

(21) Appl. No.: 18/178,796

(22) Filed: Mar. 6, 2023

(65) Prior Publication Data

US 2023/0200644 A1     Jun. 29, 2023

Related U.S. Application Data

(63) Continuation-in-part of application No. 17/741,085, filed on May 10, 2022, now Pat. No. 11,596,302.

(Continued)

(51) Int. Cl.
*A61B 3/14*        (2006.01)
*A61B 5/00*        (2006.01)

(52) U.S. Cl.
CPC .............. *A61B 3/14* (2013.01); *A61B 5/6898* (2013.01)

(58) Field of Classification Search
CPC ....... A61B 3/14; A61B 5/6898; A61B 5/4064; A61B 5/6814; A61B 5/6821; A61B 3/0041; A61B 3/032

(Continued)

(56) References Cited

U.S. PATENT DOCUMENTS

| | | |
|---|---|---|
| 6,003,991 A | 12/1999 | Viirre |
| 9,788,714 B2 | 10/2017 | Krueger |

(Continued)

FOREIGN PATENT DOCUMENTS

| | | |
|---|---|---|
| CA | 3117117 A1 | 4/2020 |
| CN | 105718046 A | 6/2016 |

(Continued)

OTHER PUBLICATIONS

Non-final Office Action issued on corresponding U.S. Appl. No. 17/741,085 dated Jul. 27, 2022, 10 pages.

(Continued)

*Primary Examiner* — Mohammed A Hasan
(74) *Attorney, Agent, or Firm* — DENTONS DAVIS BROWN PC; Matthew Warner-Blankenship

(57)                ABSTRACT

Disclosed is an eye examination apparatus for use with a smartphone or other portable electronic device. The eye examination apparatus has a body having a first eye opening and a second eye opening for a user to see into the eye examination apparatus using two eyes. In accordance with an embodiment of the disclosure, the eye examination apparatus has a coupling for receiving a smartphone having a display and a camera and for holding the smartphone in a predefined position in relation to the body, such that the camera of the smartphone is positioned to acquire ophthalmic images through the first eye opening, and the display of the smartphone is viewable through the second eye opening. In this manner, it is possible for the user to have an eye examination performed remotely outside of a clinician's office without specialized equipment by instead using their own smartphone.

20 Claims, 23 Drawing Sheets

Related U.S. Application Data

(60) Provisional application No. 63/209,227, filed on Jun. 10, 2021, provisional application No. 63/186,983, filed on May 11, 2021.

(58) Field of Classification Search
USPC ......................................................... 351/206
See application file for complete search history.

(56) References Cited

U.S. PATENT DOCUMENTS

| | | | |
|---|---|---|---|
| 10,231,614 B2 | 3/2019 | Krueger | |
| 10,758,121 B2 | 9/2020 | Rennaker et al. | |
| 10,832,051 B1 | 11/2020 | Trail et al. | |
| 11,596,302 B2 * | 3/2023 | Mansouri | A61B 3/0008 |
| 2005/0174536 A1 * | 8/2005 | Hanaki | A61B 3/0091 |
| | | | 351/204 |
| 2013/0335543 A1 | 12/2013 | Hilkes et al. | |
| 2016/0262608 A1 | 9/2016 | Krueger | |
| 2017/0000330 A1 | 1/2017 | Samec et al. | |
| 2017/0007115 A1 | 1/2017 | Samec et al. | |
| 2017/0065167 A1 * | 3/2017 | Walmsley | A61B 3/032 |
| 2017/0150882 A1 | 6/2017 | Lindig et al. | |
| 2017/0219826 A1 | 8/2017 | Haseltine | |
| 2017/0325675 A1 | 11/2017 | Liu et al. | |
| 2018/0220889 A1 | 8/2018 | Dirghangi et al. | |
| 2018/0263488 A1 | 9/2018 | Pamplona | |
| 2018/0279870 A1 | 10/2018 | Walsh et al. | |
| 2019/0117064 A1 | 4/2019 | Fletcher et al. | |
| 2019/0125179 A1 | 5/2019 | Xu et al. | |
| 2019/0133435 A1 | 5/2019 | Browne et al. | |
| 2019/0167095 A1 | 6/2019 | Krueger | |
| 2020/0008667 A1 | 1/2020 | Raviv et al. | |
| 2020/0029811 A1 | 1/2020 | Fried et al. | |
| 2020/0196863 A1 | 6/2020 | Anderson et al. | |
| 2020/0397288 A1 | 12/2020 | Zidan | |
| 2021/0059522 A1 | 3/2021 | Shimizu et al. | |
| 2021/0290056 A1 | 9/2021 | Karandikar et al. | |
| 2021/0315453 A1 | 10/2021 | Jeon | |

FOREIGN PATENT DOCUMENTS

| | | | |
|---|---|---|---|
| CN | 110742575 A | 2/2020 |
| EP | 3437549 A1 | 2/2019 |
| EP | 3564731 A1 | 11/2019 |
| JP | 2019141697 A | 8/2019 |
| JP | 2020006002 A | 1/2020 |
| JP | 20200006002 A | 1/2020 |
| KR | 10-2017-0048752 A | 5/2017 |
| KR | 101966164 B1 | 4/2019 |
| KR | 20200088630 A | 7/2020 |
| WO | 2017127494 A1 | 7/2017 |
| WO | 2017196403 A1 | 11/2017 |
| WO | 2019046492 A1 | 3/2019 |
| WO | 2020086693 A1 | 4/2020 |

OTHER PUBLICATIONS

International Search Report and Written Opinion from corresponding International Application No. PCT/CA2022/050735 dated Aug. 11, 2022, 7 pages.

International Search Report and Written Opinion from corresponding International Application No. PCT/CA2022/050736 dated Aug. 12, 2022, 10 pages.

Taghdiri F, Chung J, Irwin S, Multani N, Tarazi A, Ebraheem A, et al. Decreased Number of Self-Paced Saccades in Post-Concussion Syndrome Associated with Higher Symptom Burden and Reduced White Matter Integrity. J Neurotrauma. Mar. 1, 2018; 35(5):719-29.

Heitger MH, Jones RD, Macleod AD, Snell DL, Frampton CM, Anderson TJ. Impaired eye movements in post- concussion syndrome indicate suboptimal brain function beyond the influence of depression, malingering or intellectual ability. Brain. Oct. 2009; 132(Pt 10):2850-70.

Heitger MH, Anderson TJ, Jones RD, Dalrymple-Alford JC, Frampton CM, Ardagh MW. Eye movement and visuomotor arm movement deficits following mild closed head injury. Brain. Mar. 2004; 127(Pt 3):575-90.

Schretlen DJ, Shapiro AM. A quantitative review of the effects of traumatic brain injury on cognitive functioning. Int Rev Psychiatry. Nov. 2003; 15(4):341-9.

Liversedge SP, Findlay JM. Saccadic eye movements and cognition. Trends Cogn Sci (Regul Ed). Jan. 2000; 4(1):6-14.

Brunye TT, Drew T, Weaver DL, Elmore JG. A review of eye tracking for understanding and improving diagnostic interpretation. Cogn Research. Feb. 22, 2019; 4(1):7.

Hansen DW, Ji Q. In the eye of the beholder: a survey of models for eyes and gaze. IEEE Trans Pattern Anal Mach Intell. Mar. 2010; 32(3):478-500.

Holmqvist K, Nystrom M, Andersson R, Dewhurst R, Van de Weijer J. Eye Tracking: A Comprehensive Guide To Methods And Measures. Jan. 1, 2011.

Cipresso P, Giglioli IAC, Raya MA, Riva G. The past, present, and future of virtual and augmented reality research: A network and cluster analysis of the literature. Front Psychol. Nov. 6, 2018; 9:2086.

Serra A, Leigh RJ. Diagnostic value of nystagmus: spontaneous and induced ocular oscillations. J Neurol Neurosurg Psychiatr. Dec. 2002; 73(6):615-8.

Anders MR, Donatelli R, Nash J, Bascharon R. Evidence of dynamic visual acuity impairment in asymptomatic mixed martial arts fighters. Concussion. Nov. 2017; 2(3):CNC41.

Halmagyi GM, Chen L, MacDougall HG, Weber KP, McGarvie LA, Curthoys IS. The video head impulse test. Front Neurol. Jun. 9, 2017; 8:258.

Lemos J, Eggenberger E. Saccadic intrusions: review and update. Curr Opin Neurol. Feb. 2013; 26(1):59-66.

Poletti M, Intoy J, Rucci M. Accuracy and precision of small saccades. Sci Rep. Sep. 30, 2020; 10(1):16097.

Di Stasi LL, Catena A, Cañas JJ, Macknik SL, Martinez-Conde S. Saccadic velocity as an arousal index in naturalistic tasks. Neurosci Biobehav Rev. Jun. 2013; 37(5):968-75.

Xu-Wilson M, Zee DS, Shadmehr R. The intrinsic value of visual information affects saccade velocities. Exp Brain Res. Jul. 2009; 196(4):475-81.

Wong AMF. Eye Movements; Saccades. Encyclopedia of the neurological sciences. Elsevier, 2014. p. 249-51.

Walker J. Human saccadic eye movements. Scholarpedia. 2012; 7(7):5095.

Hunfalvay M, Roberts C-M, Murray N, Tyagi A, Kelly H, Bolte T. Horizontal and vertical self-paced saccades as a diagnostic marker of traumatic brain injury. Concussion. Jul. 25, 2019; 4(1):CNC60.

Cifu DX, Wares JR, Hoke KW, Wetzel PA, Gitchel G, Carne W. Differential eye movements in mild traumatic brain Injury versus normal controls. J Head Trauma Rehabil. Feb. 2015; 30(1):21-8.

Williams IM, Ponsford JL, Gibson KL, Mulhall LE, Curran CA, Abel LA. Cerebral control of saccades and heuropsychological test results after head injury. J Clin Neurosci. Apr. 1997, 4(2): 186-96.

Termsarasab P, Thammongkolchai T, Rucker JC, Frucht SJ. The diagnostic value of saccades in movement disorder patients: a practical guide and review. J Clin Mov Disord. Oct. 1, 20155; 2:14.

Takahashi M, Shinoda Y. Brain Stem Neural Circuits of Horizontal and Vertical Saccade Systems and their Frame of Reference. Neuroscience. Nov. 1, 20180; 392:281-328.

Purves D, Augustine GJ, Fitzpatrick D, Katz LC, LaMantia A-S, McNamara JO, et al. Types of Eye Movements and Their Functions. 2001.

Woods AJ. Crosstalk in stereoscopic displays: a review. J Electron Imaging. Dec. 5, 2012; 21(4):040902.

DeValois K, Webster M. Color vision. Scholarpedia. 2011; 6(4):3073.

Knox Paul, "The parameters of eye movement", accessed Dec. 2020, www.docenti.unina.it/webdocenti-be/allegati/ materiale didattico/ 412703.

Pupillary reflex - Wikipedia. McGraw-Hill; 2012.

Mahanama, Bhanuka et al., "Eye Movement and Pupil Measures: A Review", frontiers in Computer Science. Jan. 11, 2022; vol. 3: 1-22.

(56) References Cited

OTHER PUBLICATIONS

Foulsham, T., "Eye movements and their functions in everyday tasks", Eye (2015) 29, 196-199.

Leigh, R. John, Zee, David S. The neurology of eye movements. 3rd edition. 657 pages. Oxford University Press: 1999.

First Office Action issued on corresponding Chinese Patent Application No. 2022800331365, dated May 16, 2026, 10 pages.

* cited by examiner

200

134

129    127

133

128

200

134

133    133

132

175

127

EYE EXAMINATION APPARATUS FOR USE WITH A SMARTPHONE

CROSS REFERENCE TO RELATED APPLICATIONS

This patent application is a continuation-in-part of U.S. patent application Ser. No. 17/741,085 filed May 10, 2022, which in turn claims priority to U.S. provisional patent application No. 63/186,983 filed May 11, 2021 and U.S. provisional patent application No. 63/209,227 filed Jun. 10, 2021, all of which are incorporated by reference herein in their entirety.

FIELD OF THE DISCLOSURE

This disclosure relates to eye examination apparatuses for vision assessment and diagnostic purposes.

BACKGROUND

Every year, thousands of people suffer from brain and eye diseases, such as concussion for example. When a person becomes injured, it is prudent to assess whether the person is suffering from concussion or showing any other vision impairment symptoms. Portable vision diagnostic devices can help assess whether individuals are injured and/or concussed, with a view to treating those that are injured and/or concussed while enabling others to return to their normal activities.

In underprivileged areas and countries, where access to a specialist is either difficult or impossible, portable eye exam devices are useful to provide eye-care and vision assessment options to identify life or vision-threatening diseases that should receive immediate medical attention from benign eye conditions that are not medical emergencies. Additionally, such convenient eye and vision assessments could help seniors and physically challenged individuals who face difficulty travelling to a physician's clinic. Eye and vision assessment devices can facilitate convenient eye examinations from anywhere in the world. They provide a plethora of benefits such as allowing users to get eye assessments from a doctor of their choice; they reduce dependence on typical eye examination setups; and they can potentially eliminate travelling to eye centres or clinics for conventional or complex eye-examinations.

Unfortunately, currently available portable eye-examination devices are either too bulky or complex to use. Some conventional devices only provide tailored solutions i.e. they identify some specific eye condition but are not useful for routine eye-checkups and vice versa. Often times it is also found that conventional devices lack an expected level of accuracy. More importantly, they fail to identify severe eye conditions (ophthalmic eye diseases) and therefore are not reliable.

SUMMARY OF THE DISCLOSURE

Disclosed is an eye examination apparatus for use with a smartphone. The eye examination apparatus has a body having a first eye opening and a second eye opening for a user to see into the eye examination apparatus using two eyes. In accordance with an embodiment, the eye examination apparatus has a coupling for receiving a smartphone having a display and a camera and for holding the smartphone in a predefined position in relation to the body, such that the camera of the smartphone is positioned to acquire ophthalmic images through the first eye opening, and the display of the smartphone is viewable through the second eye opening.

In this manner, it is possible for the user to have an eye examination performed remotely outside of a clinician's office without specialized equipment by instead using their own smartphone. This is an improvement over the currently available portable eye-examination devices. The eye examination apparatus it is relatively easy to use with one or two smartphones and therefore may be suitable for use by households, schools, paramedics, etc.

Also disclosed is a computer-implemented method of performing an eye examination. The method involves capturing, using a camera of a smartphone, a picture or video of a first eye of a user, and displaying, using a display of the smartphone, a picture or video for a second eye of the user. The computer-implemented method can be used in combination with the eye examination apparatus summarized above.

Also disclosed is a non-transitory computer readable medium having recorded thereon statements and instructions that, when executed by at least one processor, cause the at least one processor to perform a method for eye examination as summarized above.

Other aspects and features of the present disclosure will become apparent, to those ordinarily skilled in the art, upon review of the following description of the various embodiments of the disclosure.

BRIEF DESCRIPTION OF THE DRAWINGS

Embodiments will now be described with reference to the attached drawings in which:

FIG. 2b is a schematic of a sensor module of the eye examination apparatus of FIG. 2a;

FIG. 5b shows a detailed view of a portion of the IPD adjustment mechanism of FIG. 5a.

DETAILED DESCRIPTION OF EMBODIMENTS

Figure 1A:
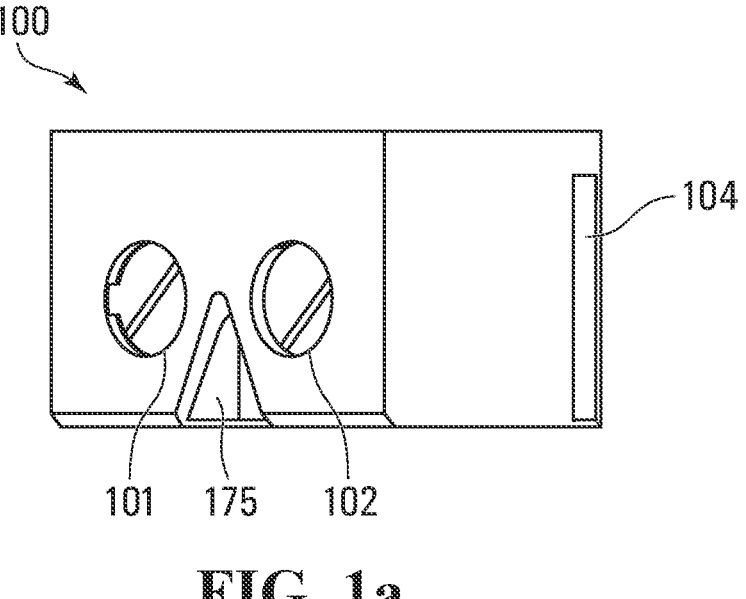
FIGS. 1a to 1d are perspective views of an eye examination apparatus that makes use of at least one smartphone.
Figure 1B:
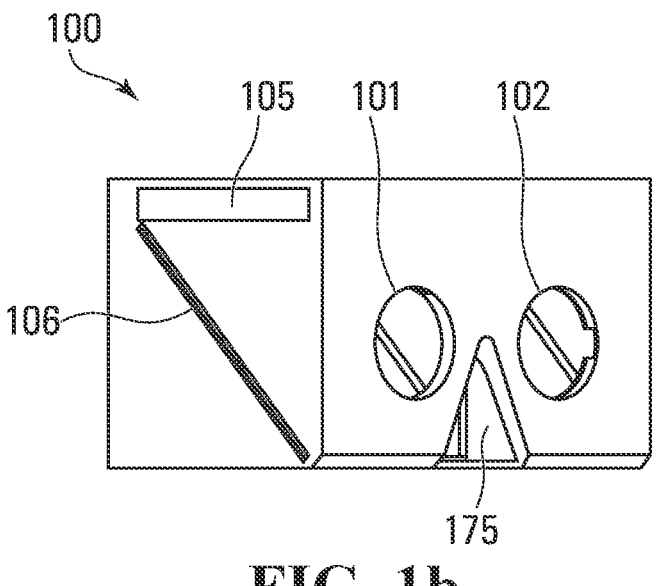
Figure 1C:
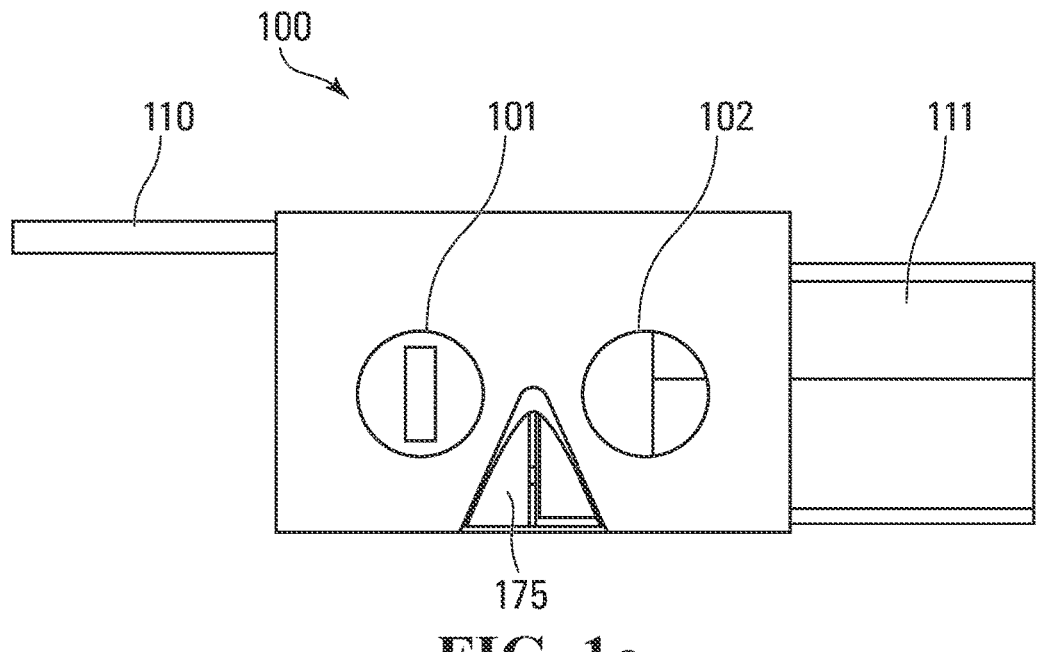
Figure 1D:
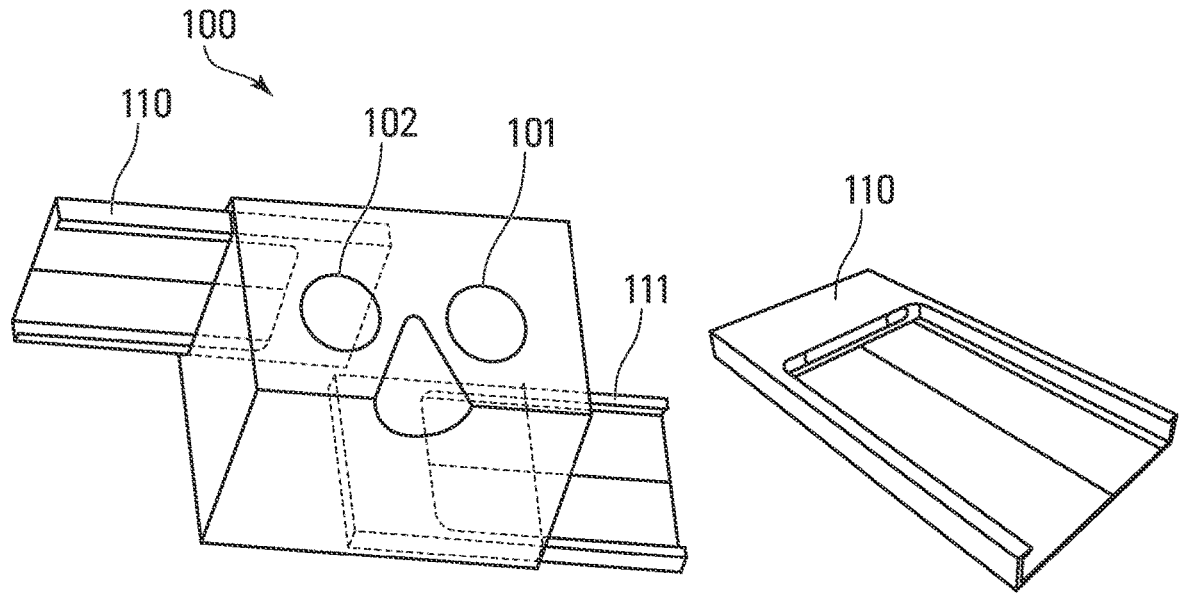

It should be understood at the outset that although illustrative implementations of one or more embodiments of the present disclosure are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

Smartphone Embodiment

Referring first to FIGS. 1a to 1d, shown are perspective views of an eye examination apparatus 100 that makes use of at least one smartphone or other portable electronic device having a display and a camera. The eye examination apparatus 100 has a closed state (FIG. 1a) in which a front cartridge 111 and an upper cartridge 110 are disposed within the eye examination apparatus 100, and received within a front slot 104 and an upper slot 105, respectively. The eye examination apparatus 100 also has an open state (FIG. 1c) in which the front cartridge 111 and/or the upper cartridge 110 are slid out or removed from the eye examination apparatus 100. The front cartridge 111 and the upper cartridge 110 are each configured to hold a smartphone and are slidably insertable into a body of the eye examination apparatus 100. The eye examination apparatus 100 has two eye openings 101 and 102.

Figure 1E:
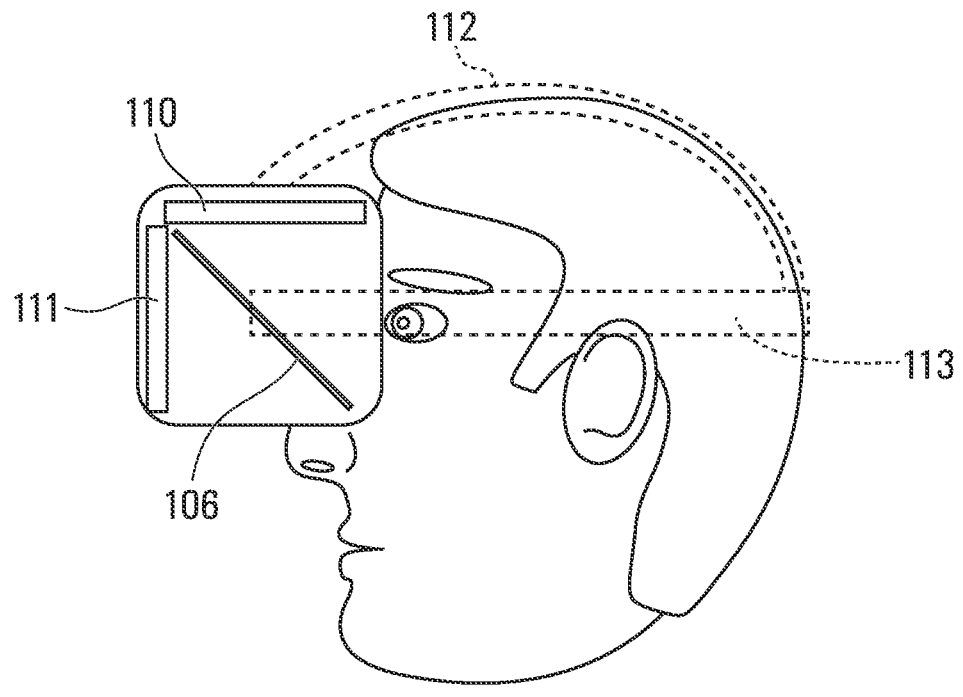
FIG. 1e is a schematic of the eye examination apparatus being worn by a user for an eye examination.

Referring now to FIG. 1e, shown is a schematic of the eye examination apparatus 100 being worn by a user for an eye examination. In some implementations, as shown in the illustrated example, the eye examination apparatus 100 has a headband 112 and 113 for securing the eye examination apparatus 100 to the user. The headband 112 and 113 can for example include an upper strap 112 and a lower strap 113 both configured to be worn on the head by the user to retain the eye examination apparatus 100 in place during the eye examination. Other securing means are possible.

In the illustrated example, the front cartridge 111 and the upper cartridge 110 each hold a smartphone (i.e. two smartphones in total) for the eye examination. As explained in further detail below, having two smartphones can enable the eye examination of both eyes simultaneously. However, it is noted that an eye examination is possible with a single smartphone, for example the smartphone in the front cartridge 111, or alternatively the smartphone in the upper cartridge 110.

Figure 1F:
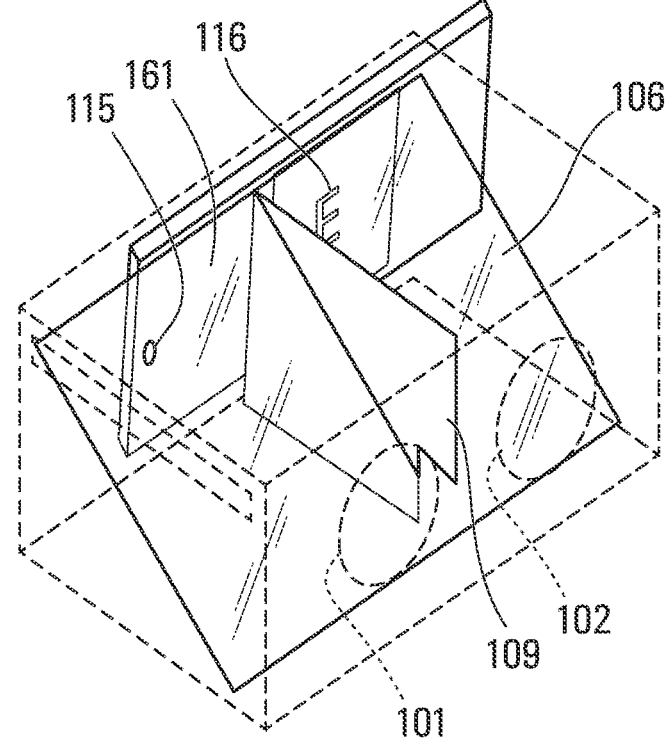
FIG. 1f is a perspective view of the eye examination apparatus equipped with a smartphone.

Referring now to FIG. 1f, shown is a perspective view of the eye examination apparatus 100 equipped with one smartphone 161. The smartphone 161 is placed in the front cartridge 111 and inserted into a front cartridge slot. Once inserted, the front cartridge 111 holds the smartphone 161 in a predefined position in relation to the body, such that a camera 115 of the smartphone 161 is positioned to acquire ophthalmic images through the first eye opening 101, and a display 116 of the smartphone 161 is viewable through the second eye opening 102. This can enable an eye examination of one eye at a time.

Figure 1G:
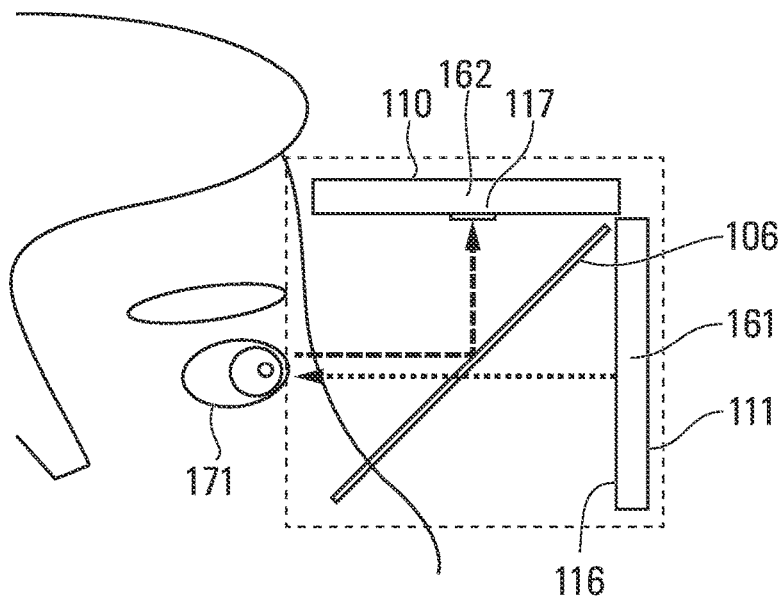
FIG. 1g is a side view of the eye examination apparatus equipped with two smartphones for an eye examination.

Referring now to FIG. 1g, shown is a side view of the eye examination apparatus 100 equipped with two smartphones 161-162 for an eye examination. As noted above, two smartphones 161-162 can be utilized to enable an eye examination of both eyes simultaneously. To support this, the eye examination apparatus 100 has a semi-transparent mirror 106 coupled to the body. With respect to the user's right eye 171, the semi-transparent mirror 106 is used to reflect light for a camera 117 of the smartphone 162 in the upper cartridge 110 while enabling light to pass through for the display of the smartphone 161 in the front cartridge 111. Conversely, with respect to the user's left eye (not shown), the semi-transparent mirror 106 is used to reflect light for a display of the smartphone in the upper cartridge 110 while enabling light to pass through for the camera of the smartphone 162 in the upper cartridge 110.

Each smartphone 161-162 functions as a DCS (Display Camera Set). In some implementations, the DCS 161 in the front cartridge 111 is designed as a primary DCS while the DCS 162 in the upper cartridge 110 is designed as a secondary DCS, although the opposite designation is possible. The camera 117 of the secondary DCS 162 and the display 116 of the primary DCS 161 are used for the user's right eye 171, while the camera 115 of the primary DCS 161 and the display (not shown) of the secondary DCS 162 are used for the user's left eye (not shown). Therefore, images of the right eye 171 are captured by the camera 117 of the secondary DCS 162 through a 90-degree reflection off of the semi-transparent mirror 106, while images of the left eye (not shown) are captured directly by the camera 115 of the primary DCS 161. Meanwhile, the right eye 171 can see the display 116 of the primary DCS 161 through the semi-transparent mirror 106, and the left eye (not shown) can see the display (not shown) of the secondary DCS 162 through a 90-degree reflection off of the semi-transparent mirror 106. In some implementations, the two DCSs 161-162 have software that when executed enable the two DCSs 161-162 to operate in sync and present similar images to the two eyes. In other implementations, the two DCSs 161-162 can operate independently and show different images. The two DCSs 161-162 can also present two images that are designed dichoptically and stereoscopically to present objects or scenes in depth. Other implementations are possible.

In the illustrated example, the upper cartridge 110 is configured to position the secondary DCS 162 in a top portion of the body of the eye examination apparatus 100. In other implementations, a lower cartridge (not shown) is configured to position the secondary DCS 162 in a bottom portion of the body. More generally, the eye examination apparatus 100 can have a second coupling for receiving the secondary DCS 162 and for holding the same in a predefined position in relation to the body, whether this predefined position is in the top portion of the body or in the bottom portion of the body. Operation of the eye examination apparatus 100 is not dependent on whether the secondary DCS 162 is in the top portion of the body or in the bottom portion of the body, because reflection off of the semi-transparent mirror 106 is possible from the top portion of the body and the bottom portion of the body.

As used herein, "ophthalmic images" can include eye surface images, eyelid images, optic nerve images, retina images, and/or other images relating to ophthalmology. Generally speaking, to acquire ophthalmic images using a camera, the camera would be positioned in front of a patient's eye and in line with a visual axis of the eye, or in another position provided that reflection and/or refraction of light (e.g. using a mirror and/or prism) enables the camera to similarly capture the front of the patient's eye. In either case, preferably the center of the patient's retina (i.e. macula and optic nerves) can be captured.

Figure 1H:
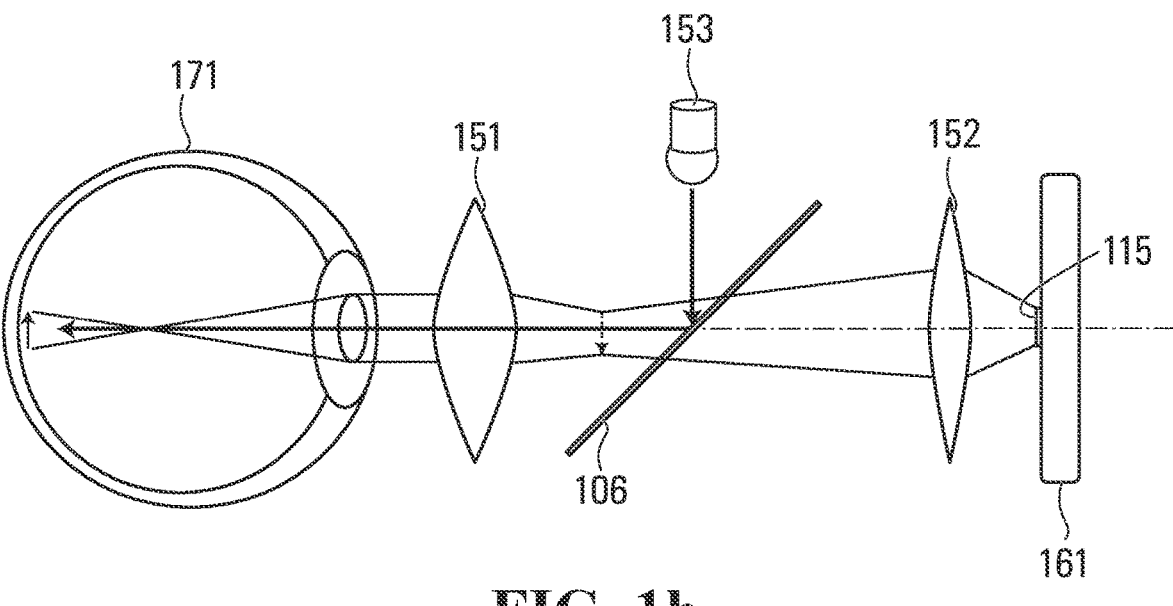
FIG. 1h is an exemplary ray diagram for the eye examination apparatus illustrating how a camera captures ophthalmic images during an eye examination.

Referring now to FIG. 1h, shown is an exemplary ray diagram for the eye examination apparatus 100 illustrating how a camera 115 captures ophthalmic images during an eye examination. In some implementations, the eye examination apparatus 100 has a pair of convex lenses 151 (for example but not limited to 50 D lenses), for the first eye opening 101 and the second eye opening 102. In some implementations, the eye examination apparatus 100 also has a second pair of convex lenses 152 (for example but not limited to 20 D lenses), for the camera 115 of the first smartphone 161 and the camera 117 of the second smartphone 162 (not shown). In some implementations, the convex lenses 151 and 152 provide enough magnification to enable a wide range of possibilities for the cameras 115 and 117 of the smartphones 161-162, as smartphones may have cameras with lower resolution than desired. However, for cameras with very high resolution, such magnification can be reduced and maybe even eliminated in which case the convex lenses 151 and 152 can be omitted. Other implementations are possible, for example but not limited to emitting, capturing and analyzing rays of light for ocular coherence tomography.

In some implementations, the eye examination apparatus 100 also has at least one light emitter 153 positioned to generate infrared or visible light out of the first eye opening 101 and the second eye opening 102 via reflection off of the semi-transparent mirror 106. In some implementations, the at least one light emitter 153 includes a first infrared emitter positioned to generate infrared light out of the first eye opening 101 and a second infrared emitter positioned to generate infrared light out of the second eye opening 102. In some implementations, infrared light can be used for lighting inside the eye examination apparatus 100, the reflection of which being captured by infrared cameras 115 and 117 on the primary and secondary DCSs 161-162. Using this functionality of the primary and secondary DCSs 161-162, the user can avoid pupil constriction and take pictures of the back of the eye 171 with an instant flashlight when the cameras 115 and 117 are focused and the picture of retina is clear. In some implementations, the at least one light emitter 153 is part of the secondary DCS 162, although other implementations are possible in which the at least one light emitter 153 is part of the first DCS 161 or separate from both the DCSs 161-162.

In the illustrated example, the camera 115 of the primary DCS 161 is positioned directly in front of the patient's eye 171 and in line with a visual axis of the eye so that the camera 115 can capture a center of a retina (i.e. macula and optic nerves) of the eye 171. In this way, the camera 115 has line of sight out of the eye opening of the eye examination apparatus 100. As used herein, "line of sight" refers to a substantially straight path without reflection within the eye examination apparatus 100, although some amount of refraction may be possible, for example through the semi-transparent mirror 106 and/or any lenses such as the convex lenses 152. Note that the camera 117 of the secondary DCS 162 is not positioned directly in front of a patient's eye. Rather, the camera 117 of the secondary DCS 162 is positioned in the upper cartridge 110, although other positions are possible. Nonetheless, by using the semi-transparent mirror 106, it is possible for the camera 117 of the secondary DCS 162 to capture the center of the retina of the patient's other eye. The eye examination apparatus 100 enables proper positioning of the primary DCS 161 and the secondary DCS 162 to acquire ophthalmic images.

According to the eye examination apparatus 100, it is possible for the user to have an eye examination performed remotely outside of a clinician's office without specialized equipment by instead using their own smartphone(s) 161-162. This is an improvement over the currently available portable eye-examination devices. The eye examination apparatus 100 does not require any high-end cameras. The eye examination apparatus 100 is relatively easy to use with one or two smartphones 161-162 and therefore may be suitable for use by households, schools, paramedics, etc.

Figure 1I:
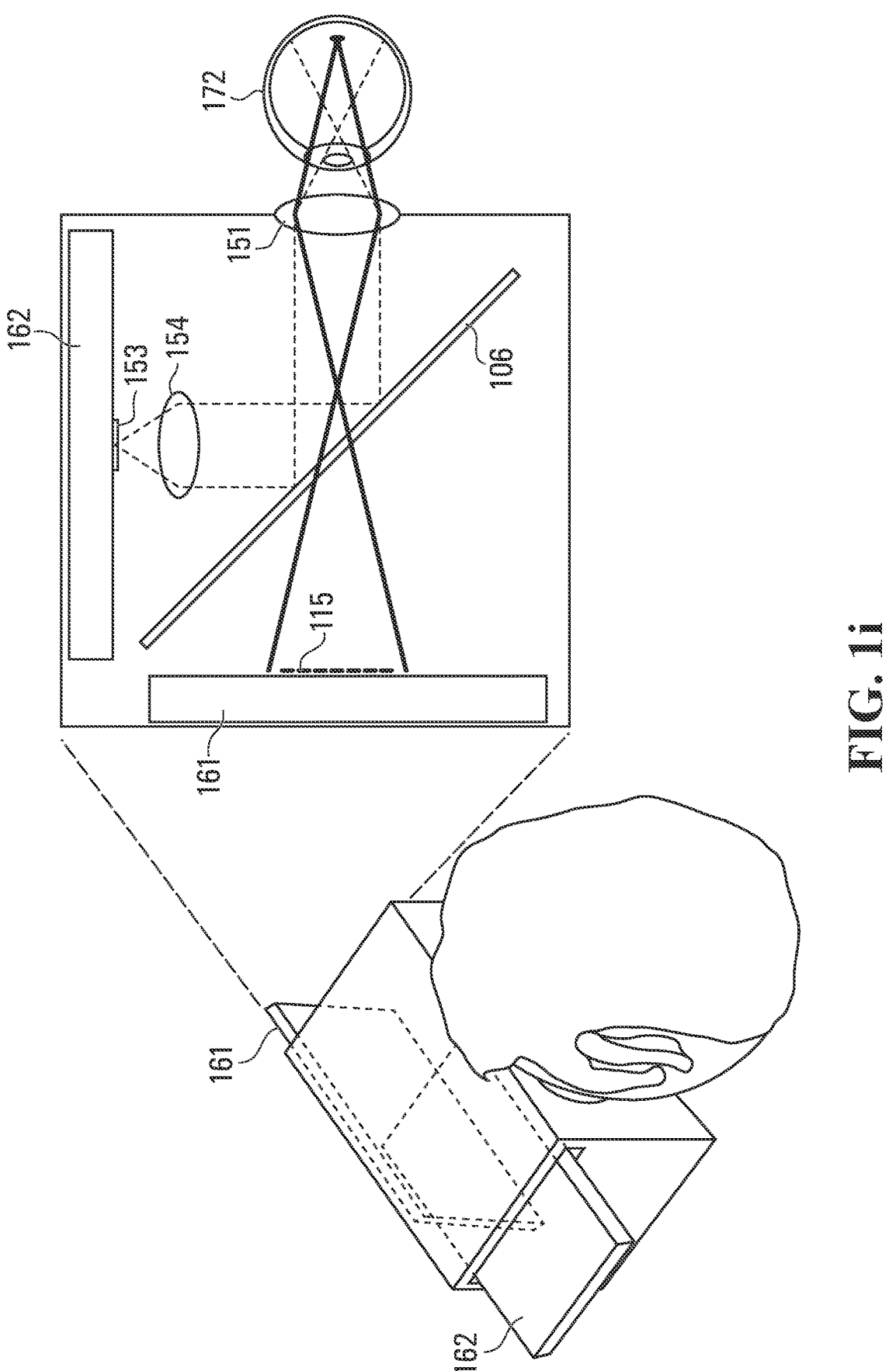
FIG. 1i is a schematic of the eye examination apparatus equipped with two smartphones and at least one condenser lens for funduscopy.

Referring now to FIG. 1i, shown is a schematic of the eye examination apparatus 100 equipped with two smartphones 161-162 and at least one condenser lens 154 for funduscopy. Funduscopy is a type of examination to check a fundus of an eye 172, including the retina and optic nerve, and often uses magnified or focused light to do so. In the illustrated example, the condenser lens 154 renders a divergent beam from the light emitter 153 of the smartphone 162 in the upper cartridge 110 into a parallel beam, which is reflected off of the semi-transparent mirror 106, and a second lens 151 condenses the parallel beam into a converging beam onto the retina of the eye 172. In alternative implementations, the condenser lens 154 renders the divergent beam into a converging beam onto the retina in which case the second lens 151 may be omitted. In some implementations, one or both of the lenses 154 and 151 are adjustable for changing focus and focal distances to adapt to different eye sizes and anatomical variations. The camera 115 of the smartphone 161 in the front cartridge 111 serves as a detector that captures light reflected from the retina of the eye 172 and passes through the semi-transparent mirror 106 to reach the camera 115. Thus, a combination of the two smartphones 161-162, the semi-transparent mirror 106, and the at least one condenser lens 154 enables funduscopy to be performed.

In the illustrated example, the light emitter 153 is from the smartphone 162 in the upper cartridge 110 and the camera 115 is from the smartphone 161 in the front cartridge 111. Additionally, or alternatively, a light emitter from the smartphone 161 in the front cartridge 111 and the camera 117 of the smartphone 162 in the upper cartridge 110 can be utilized. Both implementations are possible simultaneously, which can make it possible to perform funduscopy for both eyes, or separately.

Figure 1J:
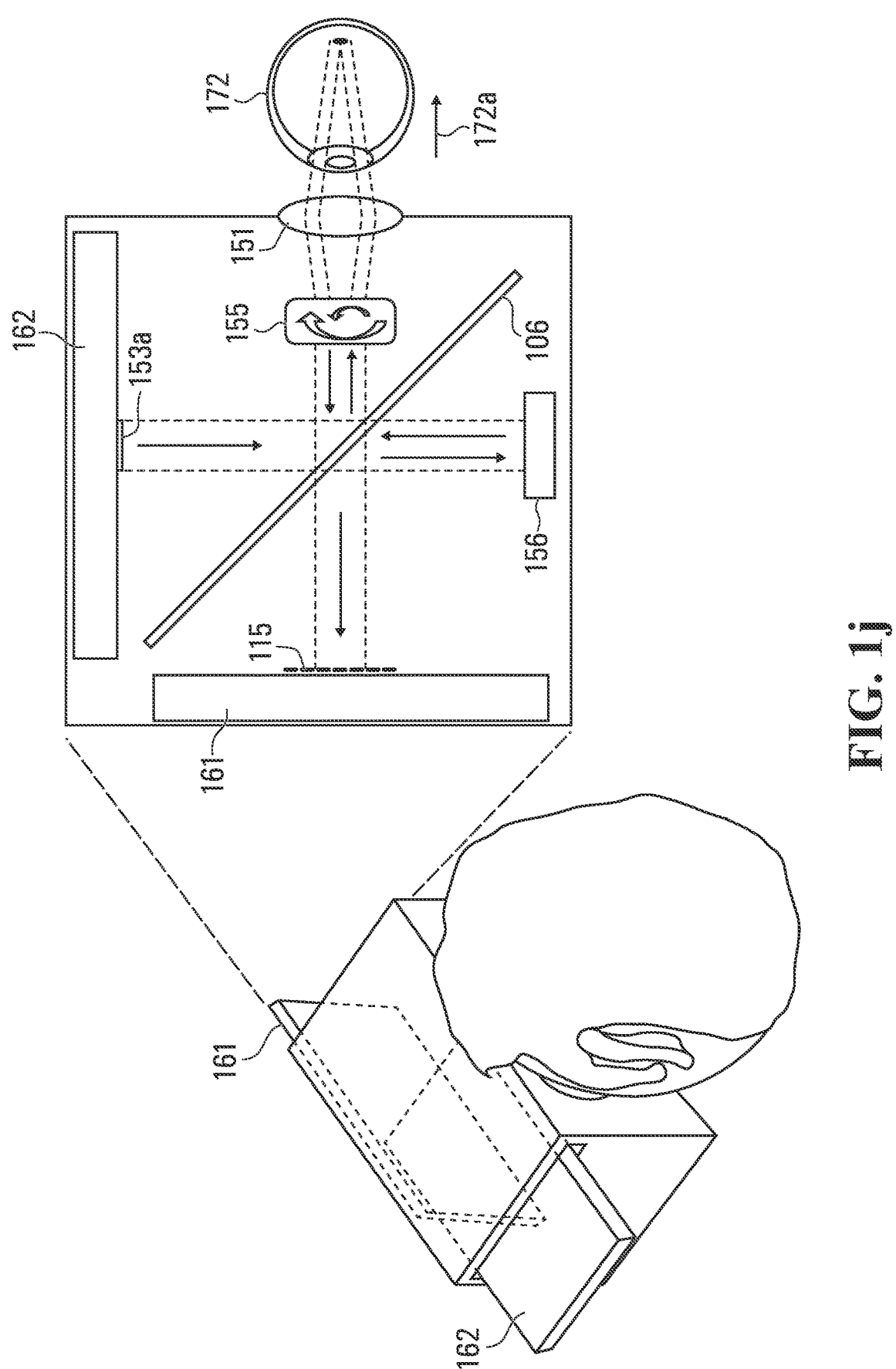
FIG. 1j is a schematic of the eye examination apparatus equipped with two smartphones and a mirror 156 for OCT (Ocular Coherence Tomography)

Referring now to FIG. 1j, shown is a schematic of the eye examination apparatus 100 equipped with two smartphones 161-162 and a mirror 156 for OCT (Ocular Coherence Tomography). Optical coherence tomography is an imaging technique that uses interferometry to capture high-resolution images based on interference of superimposed waves from a reference arm and a sample arm. In the illustrated example, a low coherence light source 153a generates low coherence light onto the semi-transparent mirror 106, which functions as a beam splitter. For the reference arm, some of the low coherence light passes through the semi-transparent mirror 106, reflects off of the mirror 156, reflects off of the semi-transparent mirror 106, and is received by the camera 115 of the smartphone 161 in the front cartridge 111. For the sample arm, the rest of the low coherence light from the low coherence light source 153a reflects off of the semi-transparent mirror 106, reflects off of the retina of the eye 172, passes through the semi-transparent mirror 106, and is received by the camera 115. The camera 115 thus receives a reference light wave from the reference arm and a sample light wave from the sample arm. The reference light wave and the sample light wave can interfere constructively (i.e. strengthening in intensity) when in phase or interfere destructively (i.e. weakening in intensity) when out of phase. Such interference between the reference light wave and the sample light wave provides imaging information which can be detected as an analog interference OCT signal. In some implementations, the camera 115 is capable of detecting NIR (Near Infrared Light) to help capture the analog interference OCT signal.

In some implementations, the sample arm includes a lens 151 to condense the low coherence light into a converging beam onto the retina of the eye 172. Furthermore, in some implementations, the sample arm includes a 2D MEMS (Microelectromechanical) mirror 155 which is an optical beam-steering device which provides a lateral scanning of the OCT. Collimated light incidents on a dual-axis galvo-mirrors of the 2D MEMS mirror 155 and is redirected to the lens 151, which operates as a telecentric objective lens. The lens 151 focuses the light onto the retina of the eye 172 and back-reflected light is received by the lens 151 and focused back through the semi-transparent mirror 106. In some implementations, the lens 151 and the 2D MEMS mirror 155 are adjustable to provide variable focus and projection.

In some implementations, the camera 115 samples the analog interference OCT signal at equal spectral intervals. Each scan produces depth information from the interference pattern by reaction at different depths in the form of an A-scan. An A-scan is a one-dimensional image of the sample (e.g. retina of the eye 172) at a specific depth. A cross-sectional image of the microstructure of the sample can be obtained by integrating multiple A-scans. In some implementations, the analog interference OCT signal which is captured is converted into a digital signal, and OCT fringe data are then processed locally on the smartphone or sent to a host computer where signal processing can be performed.

Figures 1K, 1L, 1M, 1N:
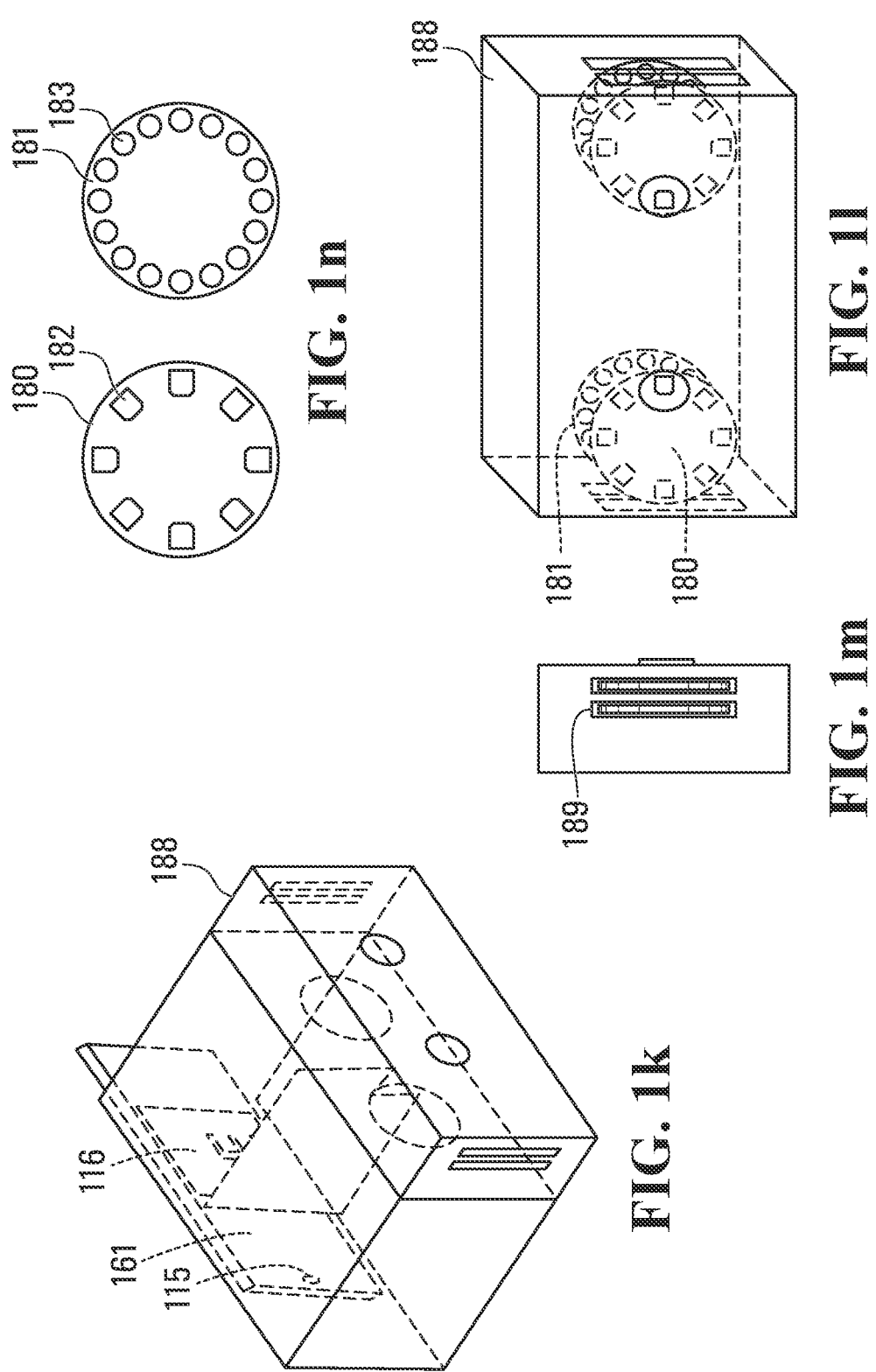
FIG. 1k is a schematic of the eye examination apparatus equipped with a refraction apparatus for refraction eye examination.
FIGS. 1l and 1m are schematics of the refraction apparatus of FIG. 1k.
FIG. 1n is a schematic of the wheels of the refraction apparatus of FIGS. 1l and 1m.

Referring now to FIG. 1k, shown is a schematic of the eye examination apparatus 100 equipped with a refraction apparatus 188 for refraction eye examination. A refraction eye examination is an eye exam that measures a person's prescription for eyeglasses or contact lenses. The refraction apparatus 188 is an optional accessory that can be attached to the eye examination apparatus 100 in order to enable refraction eye examination and subsequently detached. In some implementations, the refraction apparatus 188 attaches to the eye examination apparatus 100 using magnetic pins which are installed at the four corners on the back of the eye examination apparatus 100 and front of the refraction apparatus 188. However, other implementations for attaching the refraction apparatus 188 to the eye examination apparatus 100 are possible.

Referring now to FIGS. 1l and 1m, shown are schematics of the refraction apparatus 188 of FIG. 1k. The refraction apparatus 188 has at least two wheels 180 and 181 on each side of the refraction apparatus 188, for a total of at least four wheels. In some implementations, each wheel protrudes from the side, creating a dial 189 for the wheel that can be used to turn the wheel. In some implementations, the refraction apparatus 188 has additional wheels (not shown). More wheels may be present for further detailed variety of refraction or eye examinations or treatment delivery.

Referring now to FIG. 1n, shown is a schematic of the wheels 180 and 181 of the refraction apparatus 188 of FIGS. 1l and 1m. The first wheel 181 has spherical convex and concave lenses 183 which are used to test refraction. The second wheel 180 has cylindric convex and concave lenses 182 for astigmatism examination. Color red, green, blue, etc. filters, pinholes, any prisms, occluders, neutral density filters or any other electronically modified or physically modified or controlled lenses or filters may be used in the wheels 180 and 181.

In the illustrated example, a user can change the lenses or filters on the wheels 180 and 181 using the dials 189. In other implementations, the lenses or filters on the wheels 180 and 181 can be changed electronically via one or more actuators, which might be electronically coupled to the smartphone 161. In this way, it is possible to change the lenses or filters on the wheels 180 and 181 remotely or using the smartphone 161. In some implementations, results of the refraction eye examination are sent to a host computer for evaluation and/or to order online prescription eyeglasses or contact lenses.

The eye examination apparatus 100 described herein can be used to examine one eye at a time or two eyes at the same time. In some implementations, the eye examination apparatus 100 is equipped with at least one occluder, for example a pair of occluders. The occluders can be used selectively block light for an eye that is not being examined. Additionally, or alternatively, the occluders can be used in differentiating vision impairment. An example of this is described below with reference to FIG. 1o.

Figure 1O:
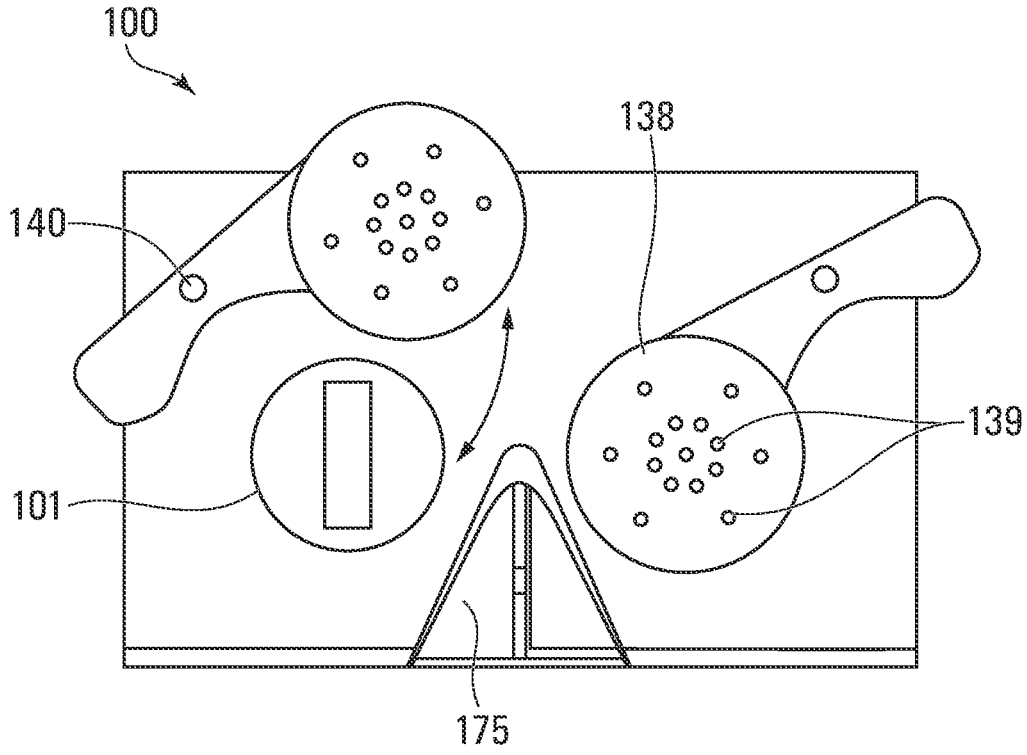
FIG. 1o is a schematic of the eye examination apparatus having a pair of occluders.

Referring now to FIG. 1o, shown is a schematic of the eye examination apparatus 100 having a pair of occluders 138. In some implementations, the occluders 138 are optionally provided as additional attachments. The occluders 138 can either slide/swipe over the lenses 101 or can be placed directly on the lenses 101. In some implementations, the occluders 138 have a plurality of pinholes 139 (for example fifteen pinholes as depicted). The pinholes 139 are configured to eliminate disorganized refracted light arrays which cause blurred vision in non-neurological eye conditions. More precisely, the pinholes 139 assist in differentiating vision impairment caused by neurological eye diseases such as multiple sclerosis, stroke, etc. versus non-neurological eye diseases such as refractive error, dry eye, etc. Moreover, the pinholes 139 are useful for testing visual acuity in cycloplegic eyes (state of the eye after paralyzing the pupil and lens muscles with specific eye drops) as they are can effectively reduce the intensity of incoming light.

In some implementations, each occluder 138 is secured in place using a pin 140 attached to the front surface of the eye examination apparatus 100, which enables it to pivot down when being used. In other implementations, the occluders 138 can be placed directly on or fitted over the lenses 101. Other implementations are possible.

In some implementations, the first eye opening 101 and the second eye opening 102 of the eye examination apparatus 100 are separate openings as depicted. However, other implementations are possible in which the first eye opening 101 and the second eye opening 102 are part of the same opening, namely a large opening that enables the user to see into the eye examination apparatus 100 using both eyes. In some implementations, the eye examination apparatus 100 has a middle wall 109 separating a left side for examining the user's left eye from a right side for examining the user's right eye.

There are many possibilities of the body of the eye examination apparatus 100. In some implementations, the body includes a plastic material. In specific implementations, the body is generated using a 3D printer. The front cartridge 111 and the upper cartridge 110 can also be formed of a plastic material and generated using a 3D printer. In specific implementations, a user can use a 3D printer to generate the eye examination apparatus 100 themselves. In other implementations, the eye examination apparatus 100 is produced and distributed to the user by a manufacturer. Note that other materials such as cardboard can be used instead of (or in addition to) plastic. Factory produced head-mounted devices are also possible. Other implementations are possible.

There are many possibilities for securing the eye examination apparatus 100 to the user. In some implementations, as described above, the eye examination apparatus 100 has a headband 112 and 113 for securing the eye examination apparatus 100 to the user. In other implementations, eye examination apparatus 100 is simply held by the user against their face. In some implementations, the eye examination apparatus 100 has a nose rest 175, which may help to facilitate the eye examination apparatus 100 to properly fit against the user's face. Other implementations are possible.

Although the illustrated examples focus on a particular type of coupling for receiving smartphone(s), it is noted that other types of coupling are possible and are within the scope of the disclosure. Any suitable coupling that is able to receive and hold a smartphone in a predefined position such that its camera can acquire ophthalmic images through the first eye opening 101 and its display is viewable through the second eye opening 102 can be employed. Snap-fit implementations and/or other fixation means are possible without sliding cartridges as depicted. Also, other positions for the couplings are possible. For example, as noted above, rather than the upper cartridge 110, the eye examination apparatus 100 could employ a lower cartridge (not shown). Other implementations are possible.

Although the illustrated examples utilize the semi-transparent mirror 106 for reflection, it is noted that a semi-transparent prism can be utilized instead. It is noted that a semi-transparent prism could cause more refraction than the semi-transparent mirror 106, depending on geometry of course. It is implementation-specific whether a semi-transparent mirror or prism is utilized. In either case, light is enabled to pass through the semi-transparent mirror or prism, generally with line or sight, albeit with some amount of refraction. In specific implementations, as shown in the illustrated examples, a semi-transparent mirror is oriented at 45-degree angle relative to the first smartphone and the second smartphone to facilitate reflections, given that the smartphones are orthogonal to one another. However, other geometries are possible and are within the scope of the disclosure.

Figure 1P:
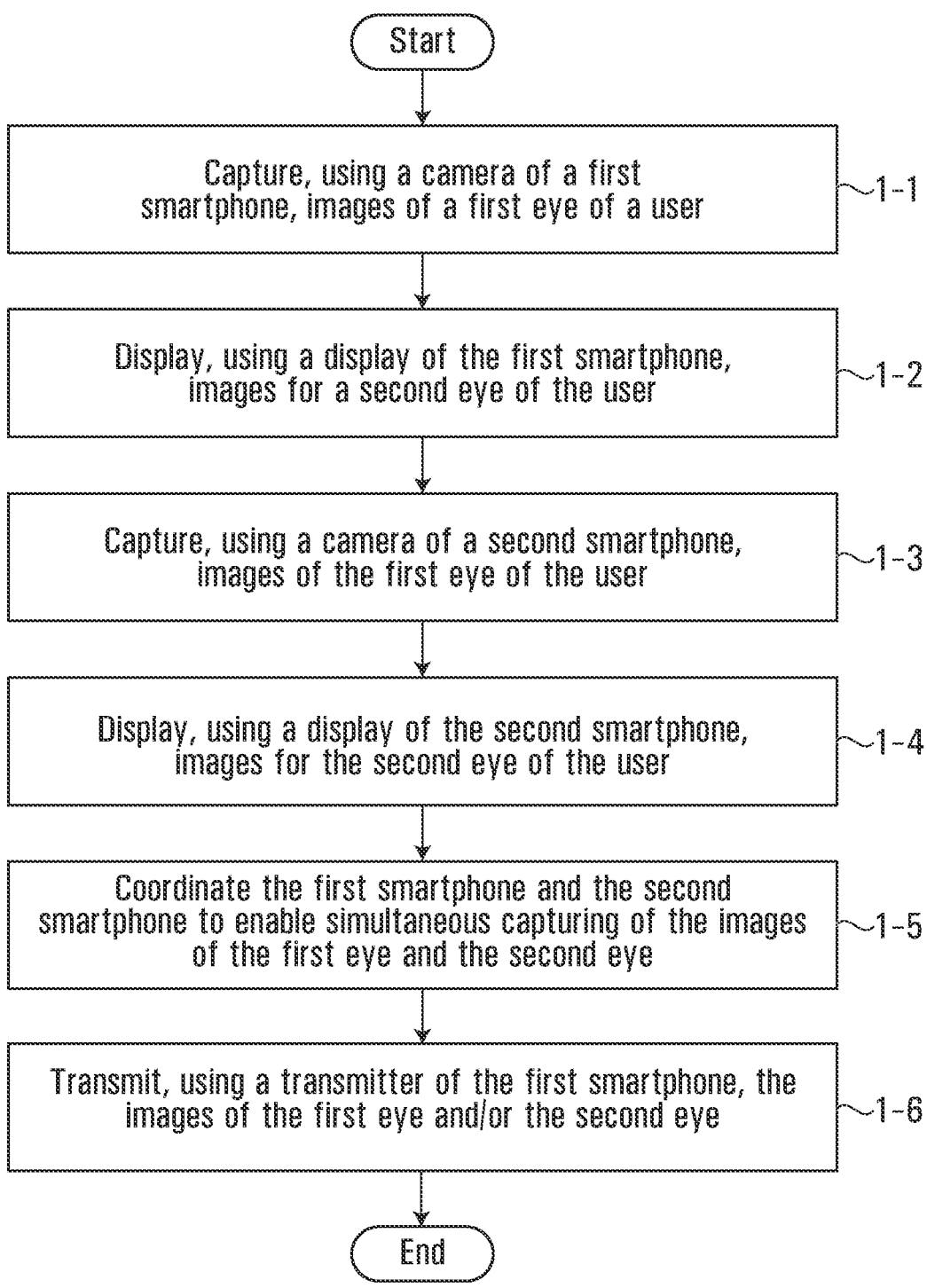
FIG. 1p is a flowchart of a computer-implemented method of performing an eye examination.

Referring now to FIG. 1*p*, shown is a flowchart of a computer-implemented method of performing an eye examination. This method can be executed by at least one processor, for example by a processor of one of the smartphones described above in relation to FIGS. 1*a* to 1*o*. In some implementations, the smartphone downloads and executes an app to enable the computer-implemented method described below.

At step 1-1, the processor captures, using a camera of the smartphone, images of a first eye of a user. At step 1-2, the processor displays, using a display of the smartphone, images for a second eye of the user. In some implementations, the computer-implemented method is performed with only one smartphone. This can enable an eye examination of one eye at a time. In other implementations, the computer-implemented method is performed with two smartphones, which can enable the eye examination of both eyes simultaneously.

In some implementations, as shown at step 1-3, the processor captures, using a camera of a second smartphone, images of the first eye of the user. In some implementations, as shown at step 1-4, the processor displays, using a display of the second smartphone, images for the second eye of the user. In some implementations, as shown at step 1-5, the processor coordinates the first smartphone and the second smartphone to enable simultaneous capturing of the images of the first eye and the second eye. This can help to facilitate the eye examination of both eyes simultaneously.

In some implementations, the first smartphone and the second smartphone each have a wireless capability such as Bluetooth radio or Wifi connections, and coordinating the first smartphone and the second smartphone involves pairing (for example using the Bluetooth radios or Wifi radios) the first smartphone with the second smartphone to form a wireless Bluetooth or Wifi connection, and coordinating the first smartphone and the second smartphone using communication over the wireless connection. Other implementations are possible.

In some implementations, the processor stores, in a memory of the first smartphone, the images of the first eye and the second eye. In other implementations, each smartphone stores its own images that have been acquired. In some implementations, as shown at step 1-6, the method involves transmitting, using a transmitter of the first smartphone, the images of the first eye and/or the second eye. The transmitted data can be sent to a clinician's office for example, such that the data can be assessed or examined by a clinician. In other implementations, each smartphone transmits its own data. Other implementations are possible.

According to the computer-implemented method, it is possible for the user to have an eye examination performed remotely outside of a clinician's office without specialized equipment by instead using their own smartphone(s). This is an improvement over the currently available portable eye-examination devices. The eye examination apparatus 100 is relatively easy to use with one or two smartphones and therefore may be suitable for use by households, schools, paramedics, etc.

In some implementations, AI (Artificial intelligence) and machine learning systems are adopted to analyze the ophthalmic images in order to recognize healthy from abnormal eye and visual structures and functions. All embodiments described herein can be equipped with this functionality. Use of AI can significantly help health professionals to narrow down a diagnosis and triage an urgent patient to emergency room or to a physician's office in a timely manner.

According to another embodiment of the disclosure, there is provided a non-transitory computer readable medium having recorded thereon statements and instructions that, when executed by at least one processor, implement a method as described herein. The non-transitory computer readable medium can for example include an SSD (Solid State Drive), a hard disk drive, a CD (Compact Disc), a DVD (Digital Video Disc), a BD (Blu-ray Disc), a memory stick, or any appropriate combination thereof.

Professional Embodiments

Figure 2A:
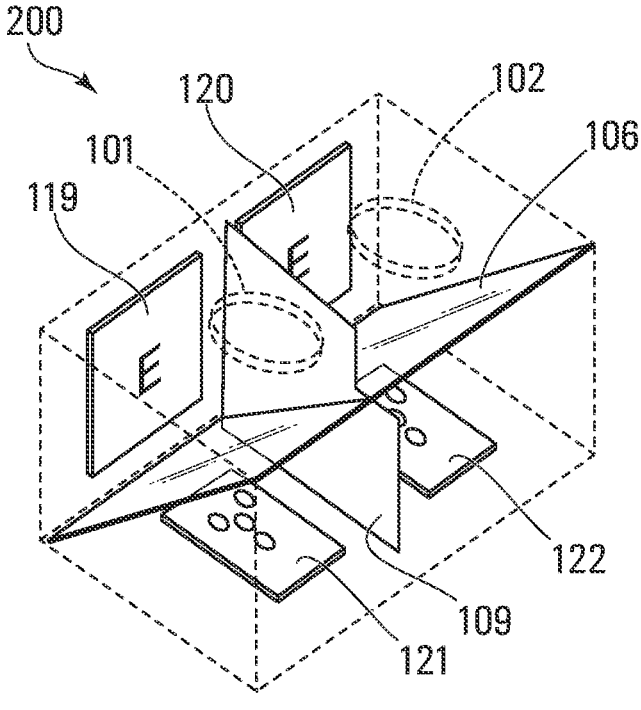
FIG. 2a is a schematic of an eye examination apparatus that can be used in a professional setting.

Referring now to FIG. 2a, shown is a schematic of an eye examination apparatus 200 that can be used in a professional setting. Unlike the eye examination apparatus 100 described with reference to FIGS. 1a to 1p, the eye examination apparatus 200 of FIG. 2a does not make use of existing smartphones, but rather is equipped with its own dedicated sensor modules 121 and 122 and at least one display 119 and 120. Still, the eye examination apparatus 200 of FIG. 2a operates using similar principles as described above for the eye examination apparatus 100 of FIGS. 1a to 1p.

There are many possibilities for the at least one display 119 and 120. In some implementations, as shown in the illustrated example, the at least one display 119 and 120 includes high-resolution display screens including a first display 119 positioned to be viewable through the first eye opening 101 and a second 120 display positioned to be viewable through the second eye opening 102. In other implementations, the at least one display 119 and 120 includes a single display having a left portion viewable through the first eye opening 101 and a right portion viewable through the second eye opening 102. Each of the displays 119 and 120 can be placed on an upper portion in the eye examination apparatus 200 as shown or on another portion such as the front wall in the eye examination apparatus 200. Other implementations are possible.

Figure 2B:
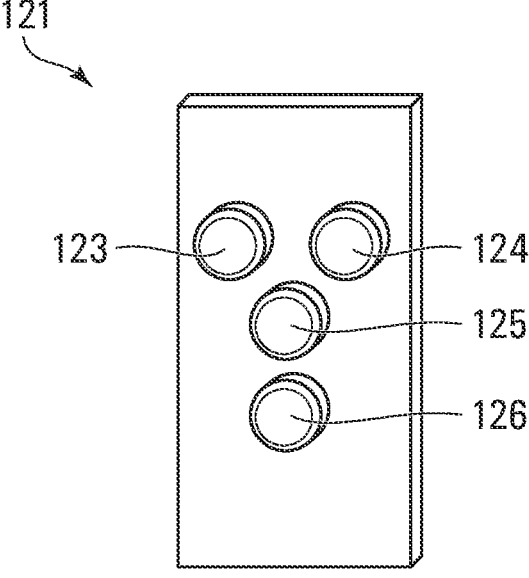
Figure 2C:
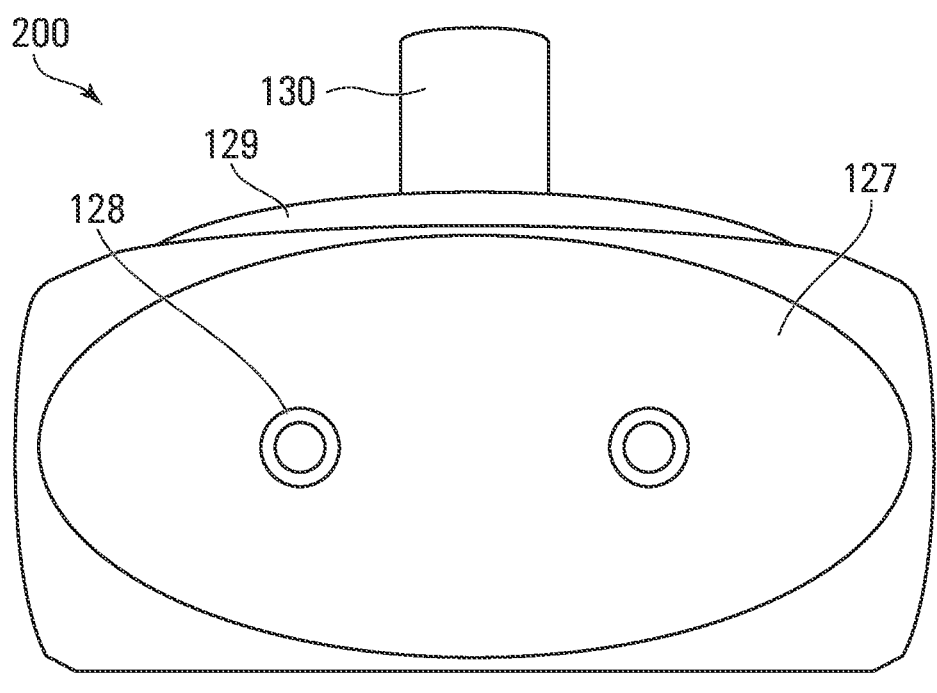
FIGS. 2c to 2f are perspective views of the eye examination apparatus implemented with a headband.
Figure 2D:
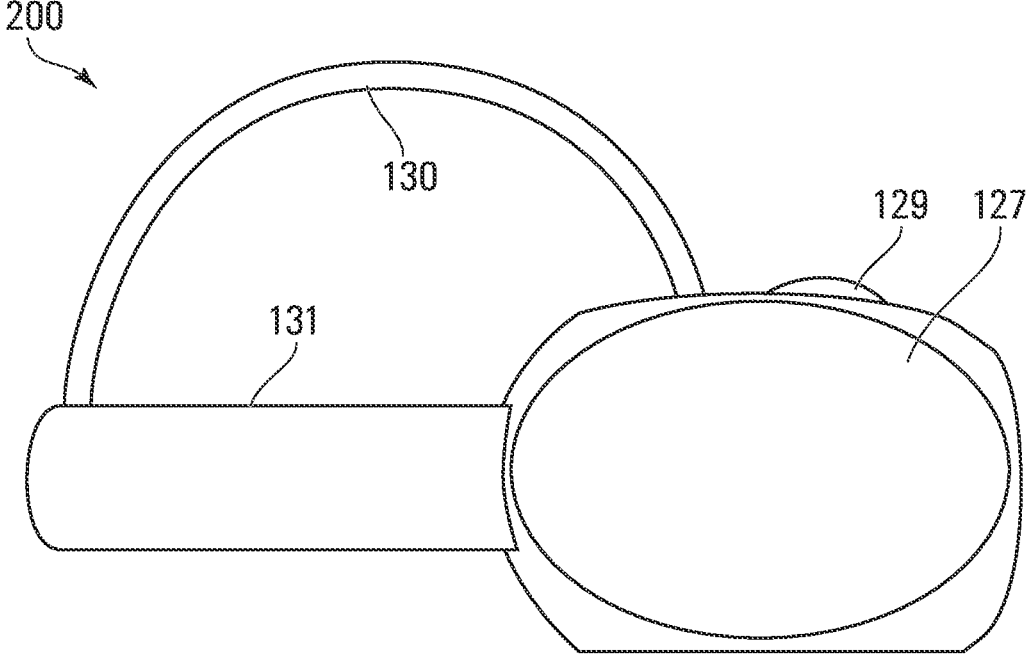
Figure 2E:
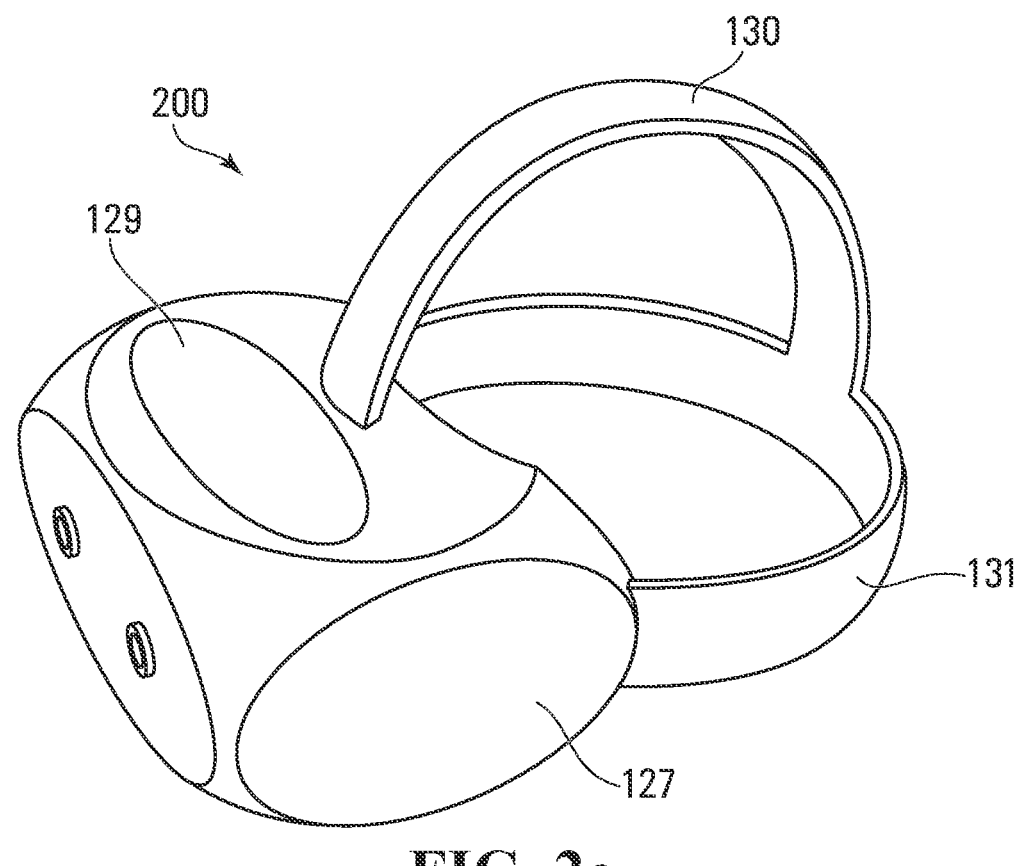
Figure 2F:
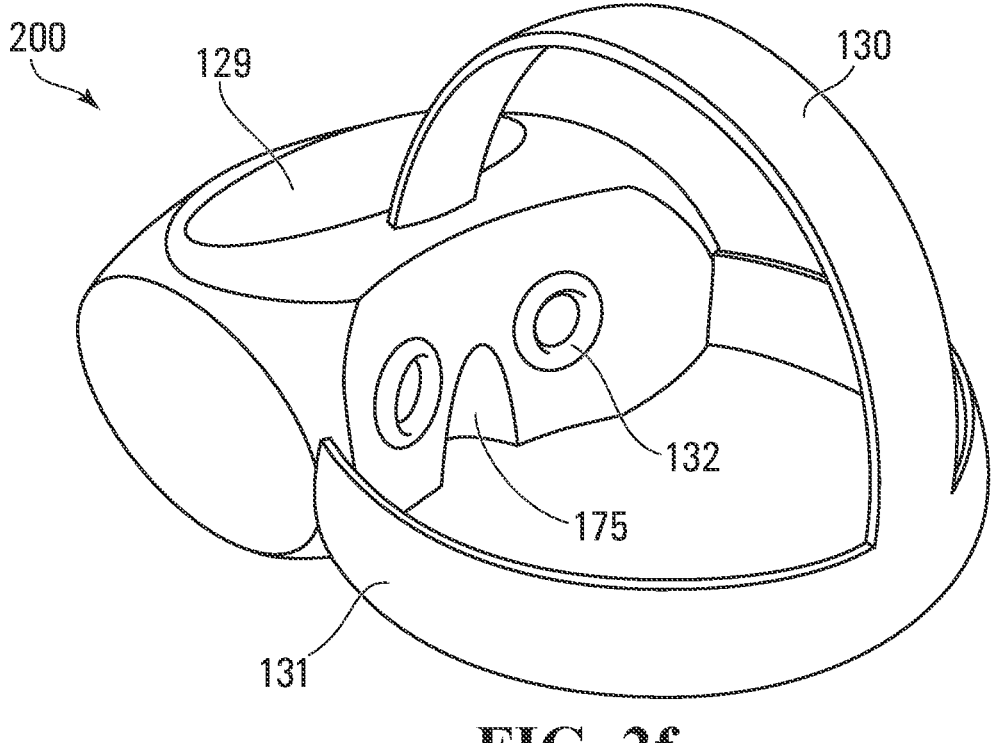
Figure 2G:
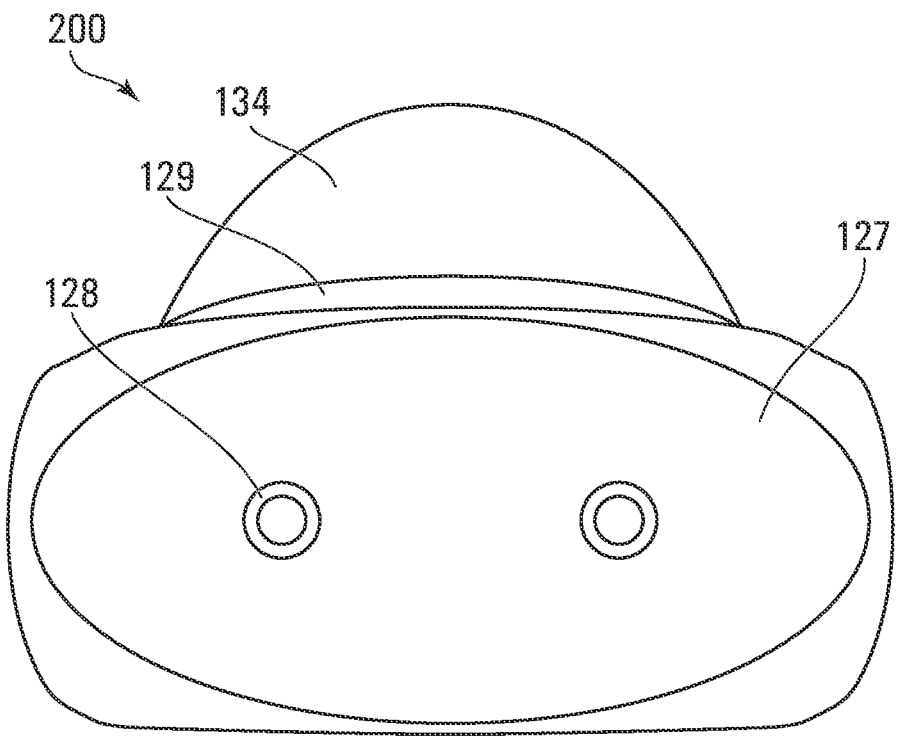
FIGS. 2g to 2l are perspective views of the eye examination apparatus implemented with a helmet.
Figure 2H:
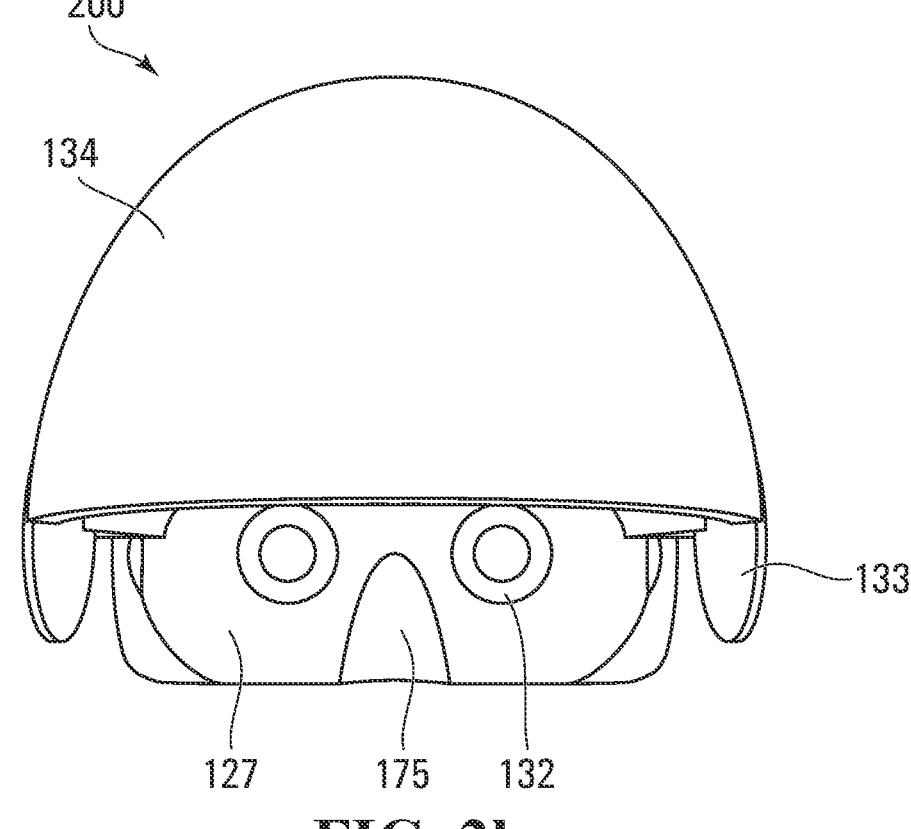
Figures 2I, 2J:
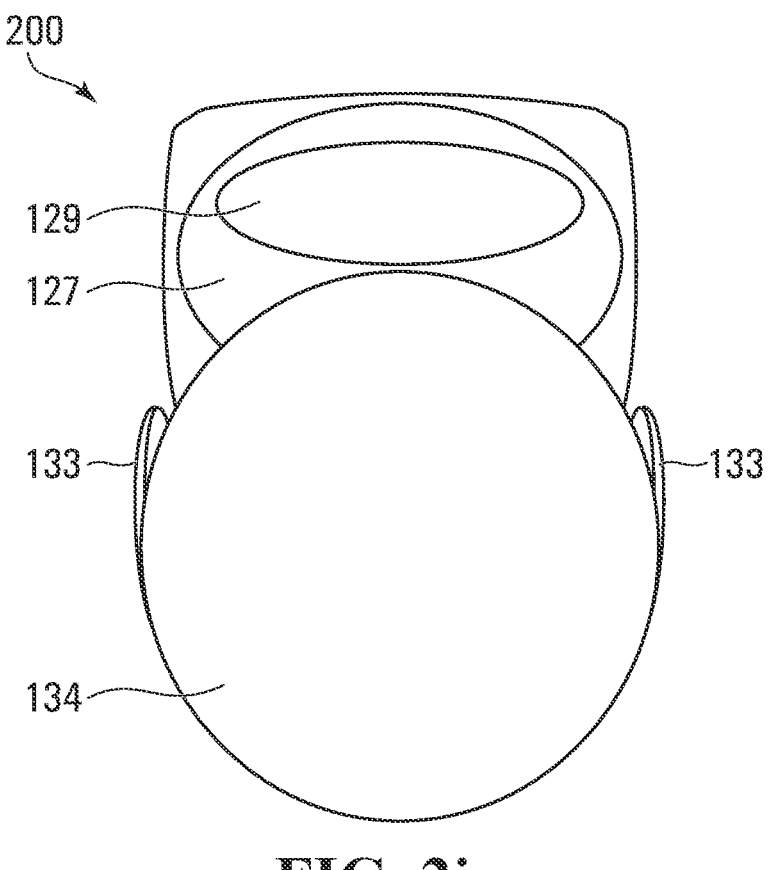
Figure 2K:
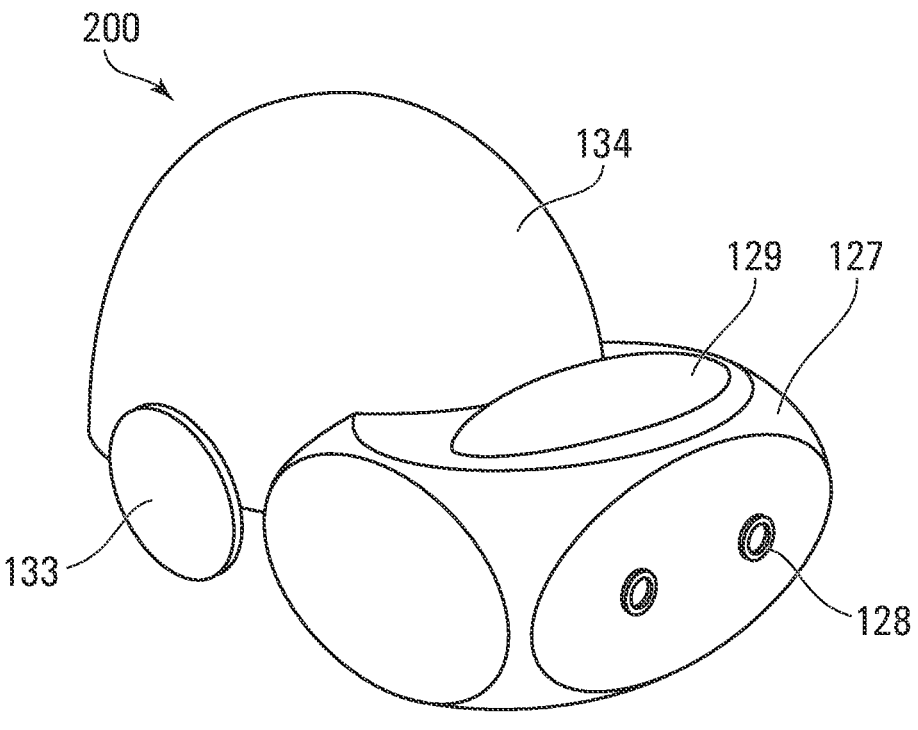
Figure 2L:
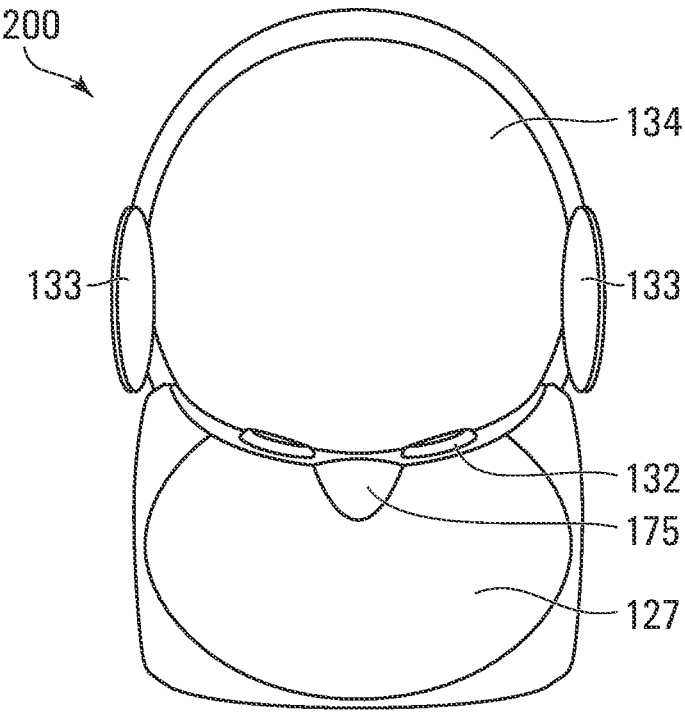

There are many possibilities for the sensor modules 121 and 122. With reference to FIG. 2b, each sensor module can for example include a pair of infrared or visible light projectors/sensors 123 and 124, at least one high resolution camera 125, and a laser emitter 126. Thus, each sensor module can have a capability of projecting laser beams, infrared light or visible light on a retina of an eye, the reflection of which being captured by the high-resolution cameras 125. The sensor modules 121 and 122 can be installed in a head-mounted device or in goggles. Other implementations are possible.

Although the eye examination apparatus 200 is depicted with the sensor modules 121 and 122, it is noted that other implementations are possible in which there are no such modules. For instance, the eye examination apparatus 200 can be provided with a first camera coupled to the body and positioned to acquire ophthalmic images through the first eye opening 101, and a second camera coupled to the body and positioned to acquire ophthalmic images through the second eye opening 102. Such cameras can be provided without the infrared projectors/sensors 123 and without the laser emitter 126. The cameras 125 can be installed in a head-mounted device or in goggles. Other implementations are possible.

In some implementations, as shown in the illustrated example, (i) a first camera (e.g. camera 125 of the sensor module 121) is positioned to acquire ophthalmic images through the first eye opening 101 via line of sight through the semi-transparent mirror 106, and the first display 119 is viewable through the first eye opening 101 via reflection off of the semi-transparent mirror 106, and (ii) a second camera (e.g. camera 125 of the sensor module 122) is positioned to acquire ophthalmic images through the second eye opening 102 via line of sight through the semi-transparent mirror 106, and the second display 120 is viewable through the second eye opening 102 via reflection off of the semi-transparent mirror 106.

In other implementations, (i) the first camera (e.g. camera 125 of the sensor module 121) is positioned to acquire ophthalmic images through the first eye opening 101 via reflection off of the semi-transparent mirror 106, and the first display 119 is viewable through the first eye opening 101 via line of sight through the semi-transparent mirror 106, and (ii) the second camera (e.g. camera 125 of the sensor module 122) is positioned to acquire ophthalmic images through the second eye opening 102 via reflection off of the semi-transparent mirror 106, and the second display 120 is viewable through the second eye opening 102 via line of sight through the semi-transparent mirror 120.

Although the illustrated example depicts a semi-transparent mirror 106 for reflection, it is noted that a semi-transparent prism can be utilized instead. It is noted that a semi-transparent prism could cause more refraction than a semi-transparent mirror, depending on geometry of course. It is implementation-specific whether a semi-transparent mirror or prism is utilized. In either case, light is enabled to pass through the semi-transparent mirror or prism, generally with line or sight, albeit with some amount of refraction. In specific implementations, as shown in the illustrated examples, the semi-transparent mirror 106 is oriented at 45-degree angle relative to the sensor modules 121 and 122 and the at least one display 119 and 120 to facilitate reflections, given that the sensor modules 121 and 122 and the at least one display 119 and 120 are orthogonal to one another. However, other geometries are possible and are within the scope of the disclosure.

In some implementations, the eye examination apparatus 200 is equipped with at least one condenser lens 154 for funduscopy, as similarly described above with reference to FIG. 1i.

In some implementations, the eye examination apparatus 200 is equipped with components for interferometry such as a low coherence light source 153a and a mirror 156 for OCT, as similarly described above with reference to FIG. 1j. In some implementations, the eye examination apparatus 200 also has a lens 151 and a 2D MEMS mirror 155, as similarly described above with reference to FIG. 1i.

In some implementations, the eye examination apparatus 200 is equipped with a refraction apparatus 188 for refraction eye examination, as similarly described above with reference to FIGS. 1k to 1n.

In some implementations, the eye examination apparatus 200 is equipped with at least one occlude, for example a pair of occludes, as similarly described above with reference to FIG. 1o.

In some implementations, the first eye opening 101 and the second eye opening 102 of the eye examination apparatus 200 are separate openings as depicted. However, other implementations are possible in which the first eye opening 101 and the second eye opening 102 are part of the same opening, namely a large opening that enables the user to see into the eye examination apparatus 100 using both eyes. In some implementations, the eye examination apparatus 200 has a middle wall 109 separating a left side for examining the user's left eye from a right side for examining the user's right eye.

Referring now to FIGS. 2c to 2f, shown are perspective views of the eye examination apparatus 200 implemented with a headband 130 and 131. In some implementations, the headband 130 and 131 includes an upper headband 130 and a lower headband 131 to enable the eye examination apparatus 200 to be worn as goggles 127. In some implementa-
tions, the eye examination apparatus 200 has a nose rest 175
for precise positioning of the goggles 127. In some imple-
mentations, the eye examination apparatus 200 is designed
in a form of head-mounted goggles to be used in professional establishments and clinics such as nursing stations,
emergency rooms, and ophthalmology, neurology or optom-
etry offices. Other implementations are possible.

In some implementations, the eye examination apparatus
200 has a processing unit for controlling the first sensor
module, the second sensor module, and the at least one
display. In some implementations, the processing unit is
configured to process ophthalmic images captured by the
high resolution cameras 125 and transmit them to a clinician
for further analysis and examination. In some implementations, the processing unit is disposed within a processor unit
housing 129 on an upper portion of the eye examination
apparatus 200. Other implementations are possible. In some
implementations, the processing unit is an MCU (Micro-
controller Unit), although other processors such as CPU
(Central Processing Unit), FPGA (Field Programmable Gate
Array), and ASIC (Application Specific Integrated Circuit)
are possible.

In some implementations, the eye examination apparatus
200 has adjustable lenses 132 for the first eye opening 101 and the second eye opening 102. The adjustable lenses 132
can enable the user to see the display screens 119 and 120
either via line of sight or via a 90-degree reflection off of the
semi-transparent mirror 106, depending on how the eye
examination apparatus 200 is implemented. The adjustable
lenses 132 also facilitate capturing images of the eyes of the
user using the high-resolution camera/scanner 125. Other
implementations are possible.

In some implementations, the eye examination apparatus
200 has at least one external sensor 128 configured to sense
an environment external to the eye examination apparatus
200, and the processing unit controls the at least one display
based on the at least one external sensor 128. In some
implementations, the at least one external sensor 128
includes a pair of external cameras 128 configured to capture
the environment external to the eye examination apparatus
200, and the processing unit generates images for the at least
one display using the pair of external cameras 128. This can
enable augmented reality.

The eye examination apparatus 200 shown in FIGS. 2c to 2f is implemented with the headband 130 and 131 for
securing the eye examination apparatus 200 to the user. In
another implementation, the eye examination apparatus 200
is implemented with a helmet to be worn by the user. An
example of this will be described below. Note that other
securing means are possible and are within the scope of the
disclosure.

Referring now to FIGS. 2g to 2l, shown are perspective
views of the eye examination apparatus 200 implemented
with a helmet 134. In some implementations, the helmet 134 includes earphones 133 as well. In some implementations,
the eye examination apparatus 200 has a nose rest 175 for
precise positioning of the helmet. In some implementations,
the eye examination apparatus 200 is designed in a form of
head-mounted helmet to be used in professional establishments and clinics such as nursing stations, emergency
rooms, and ophthalmology, neurology or optometry offices.
Other implementations are possible.

Figure 3A:
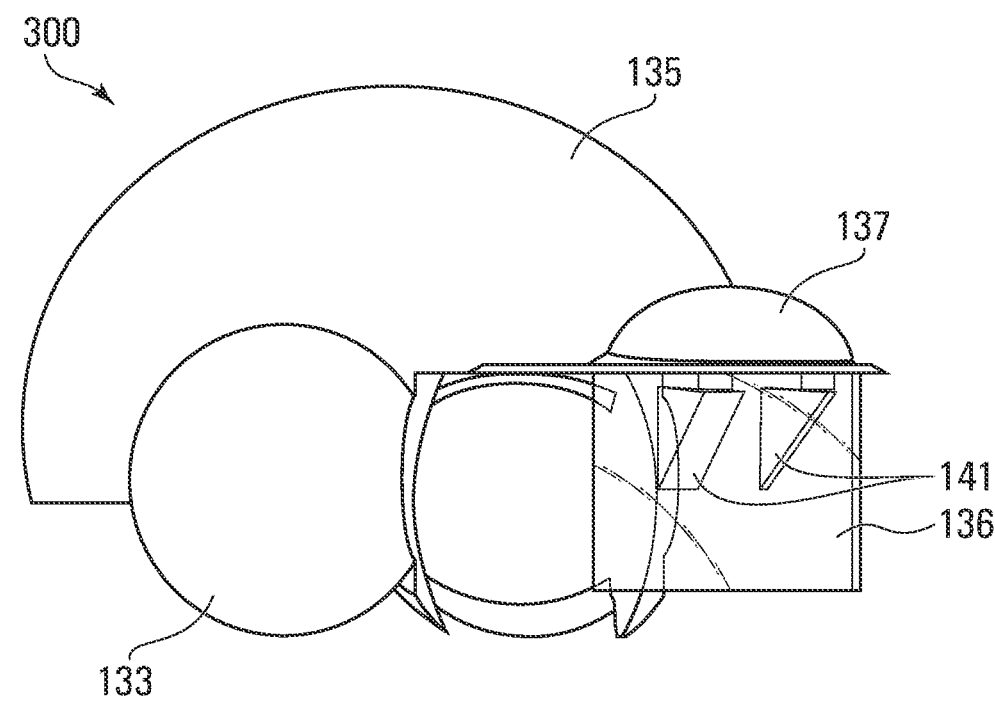
FIGS. 3a to 3c are perspective views of another eye examination apparatus that can be used in a professional setting.
Figure 3B:
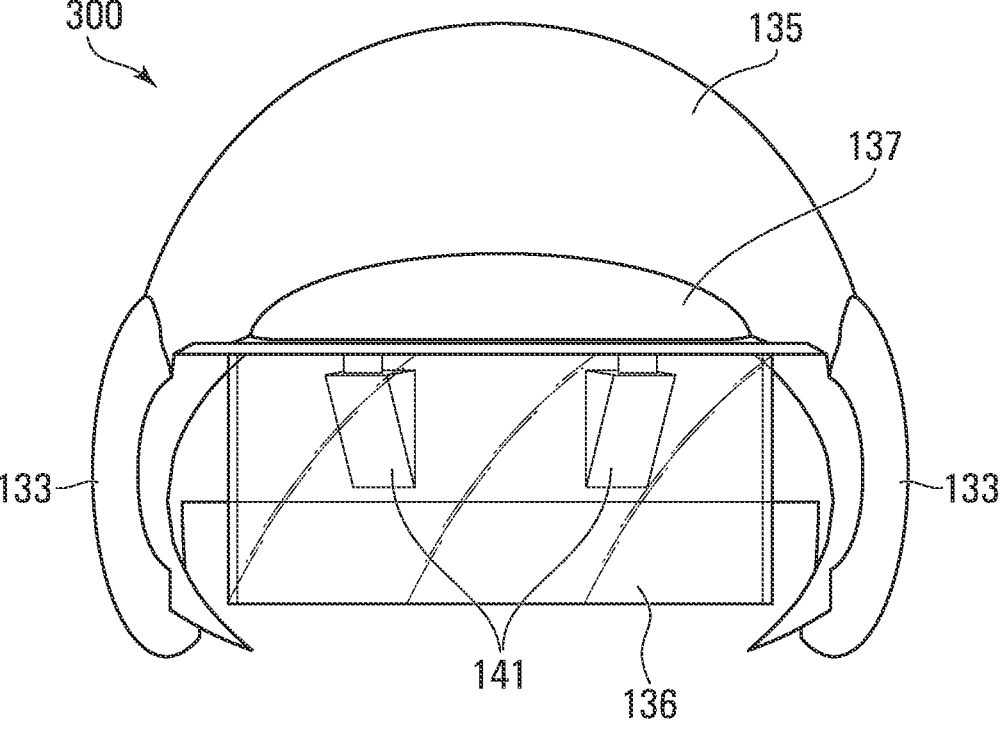
Figure 3C:
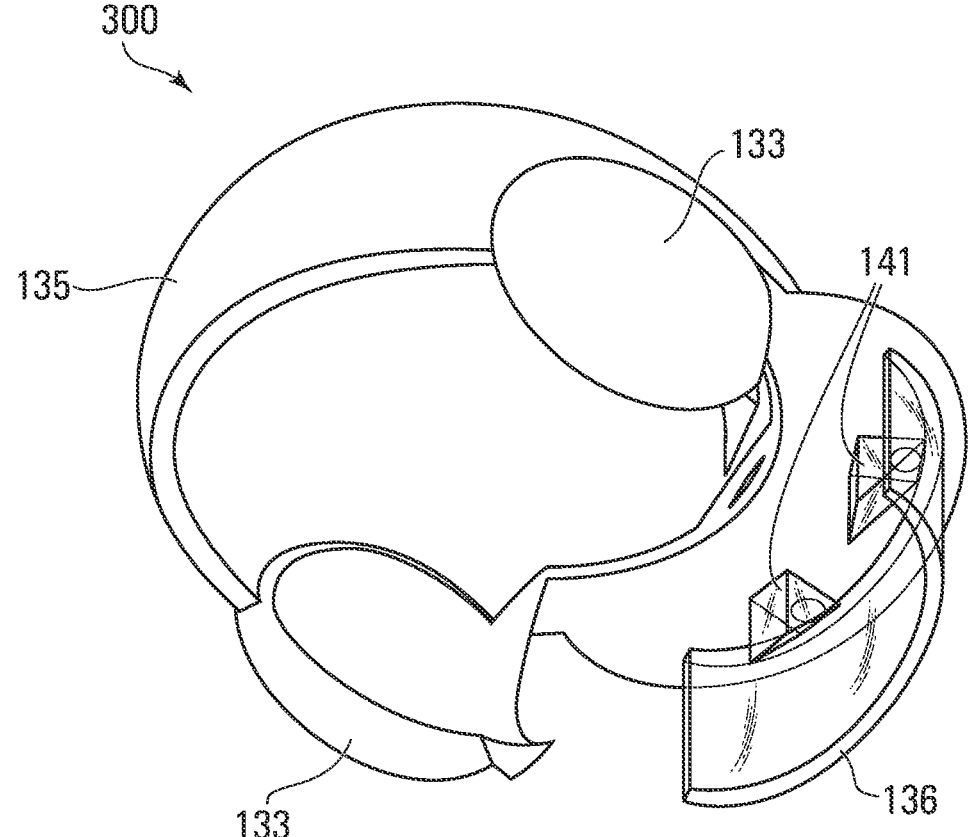

Referring now to FIGS. 3a to 3c, shown are perspective
views of another eye examination apparatus 300 that can be
used in a professional setting. Unlike the eye examination
apparatus 200 described with reference to FIGS. 2a to 2l, the eye examination apparatus 300 of FIGS. 3a to 3c does not
have eye openings for a user to see inside a region having
displays/cameras, but rather is equipped with a visor having
a transparent display 136 and camera assemblies 141. Still,
the eye examination apparatus 300 of FIGS. 3a to 3c
operates using similar principles as described above for the
eye examination apparatus 200 of FIGS. 2a to 2l.

In some implementations, the eye examination apparatus
300 is implemented with a helmet 135. In some implemen-
tations, the helmet 135 includes earphones 133 as well. In
some implementations, the eye examination apparatus 300 is
designed in a form of head-mounted helmet to be used in
professional establishments and research labs and can be
used by pilots, elite athletes, etc. Other implementations are
possible.

Each camera assembly 141 includes a camera. In some
implementations, each camera assembly 141 includes a
mirror or prism positioned to enable the camera to acquire
ophthalmic images via reflection off of the mirror or prism.
In some implementations, the camera assemblies 141 are
retractable. In the illustrated example, the camera assemblies
141 in a deployed position, which enables the camera
assemblies 141 to acquire ophthalmic images. However,
when not in use, the camera assemblies 141 can be retracted
into the eye examination apparatus 300.

In some implementations, images displayed on the trans-
parent display 136 are overlaid on a view of an environment
that can be seen through the visor, thereby enabling aug-
mented reality. In some implementations, the visor and the
transparent display 136 are also retractable. In the illustrated
example, the transparent display 136 in a deployed position,
which enables the camera assemblies 141 to acquire oph-
thalmic images. However, when not in use, the camera
assemblies 141 can be retracted into the eye examination
apparatus 300.

In some implementations, the eye examination apparatus
300 has a processing unit for the transparent display 136 and
the camera assemblies 141. In some implementations, the
processing unit is configured to process ophthalmic images
captured by the camera assemblies 141 and transmit them to
a clinician for further analysis and examination. In some
implementations, the processing unit is disposed within a
processor unit housing 137 on an upper portion of the eye
examination apparatus 300. Other implementations are pos-
sible. In some implementations, the processing unit is an
MCU, although other processors such as CPU, FPGA, and
ASIC are possible.

In some implementations, the eye examination apparatus
300 has motion and/or position sensors, and the processing
unit controls the transparent display 136 based on the motion
and/or position sensors.

In some implementations, the eye examination apparatus
300 is equipped with a refraction apparatus 188 for refrac-
tion eye examination, as similarly described above with
reference to FIGS. 1k to 1n.

In some implementations, the eye examination apparatus
300 is equipped with at least one occlude, for example a pair
of occludes, as similarly described above with reference to
FIG. 1o.

In some implementations, eye examination apparatus
according to the present disclosure may include a mecha-
nism for adjustment of interpupillary distance. Interpupil-
lary distance (IPD) is the distance between the center of the two
pupils, and is usually reported in millimeters. According to
the 2012 Anthropometric Survey of US Army Personnel (see
Gordon, C. C., Blackwell, C. L., Bradtmiller, B., Parham, J.
L., Barrientos, P., Paquette, S. P., Corner, B. D., Carson, J.

M., Venezia, J. C., Rockwell, B. M., Murcher, M., & Kristensen, S. (2014). 2012 "Anthropometric Survey of U.S. Army Personnel: Methods and Summary Statistics." Technical Report NATICK/15-007. Natick M A: U.S. Army Natick Soldier Research, Development and Engineering Center), the average IPD in men is 64.0 mm and in women is 61.7 mm; the standard deviations are 3.4 and 3.6, respectively. The IPD is smaller for children and increases with age. The IPD is increases by 4.8 mm during the second decade, by 1.7 mm during the third decade, and by 0.6 mm during the fourth and fifth decades of life (see "Normal Interpupillary Distance Values in an Iranian Population", Hamid Fesharaki, et al. J Ophthalmic Vis Res. 2012 July; 7(3): 231-234). Some implementations provide an eye examination apparatus suitable for adults, by providing the ability to adjust for IPDs in the range of 55 to 75 mm. Some implementations provide an eye examination apparatus suitable for children (e.g. aged 3-18), by providing the ability to adjust for IPDs in the range of 45 to 55 mm.

Figure 4:
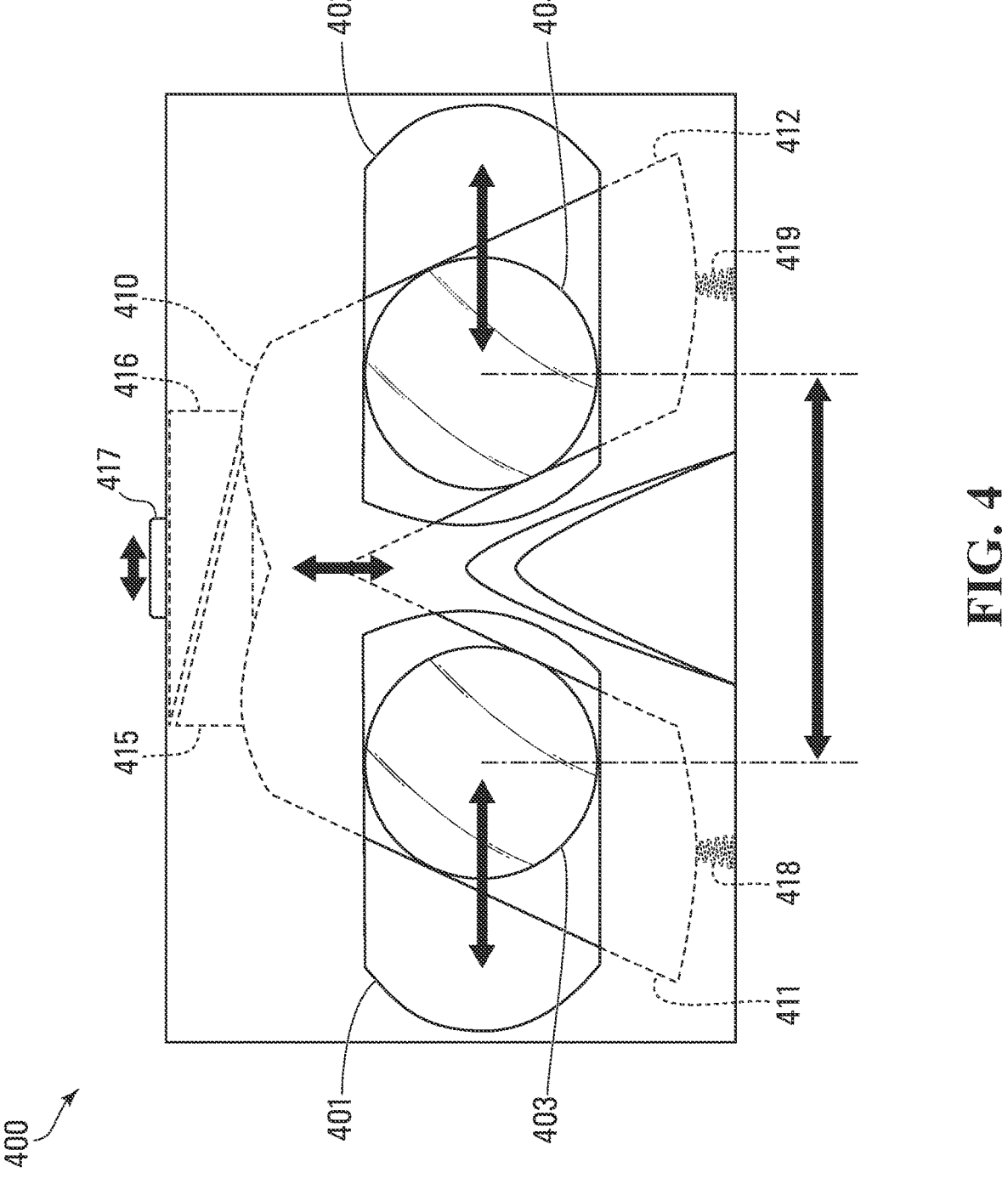
FIG. 4 shows an example IPD adjustment mechanism according to some embodiments of the present disclosure.

FIG. 4 shows an example IPD adjustment mechanism 400 according to some embodiments of the present disclosure. In the illustrated example, the IPD adjustment mechanism 400 comprises a guide member 410 that is disposed near the "rear" of the body of an eye examination apparatus (i.e. the side facing the eyes) and slidably coupled to the body to move up and down with respect thereto. The body includes openings 401 and 402 for slidably receiving lenses 403 and 404 such that each lens 403/404 is laterally movable within its respective opening 401/402. The guide member 410 defines two angles channels 411 and 412 configured to receive lenses 403 and 404 respectively, and shaped to induce lateral movement of lenses 403 and 404 in response to vertical movement of the guide member 410. In some implementations, a scale (not shown) may be printed on the body next to one of the openings 401/402 to indicate the distance between the centers of the lenses 403 and 404, as discussed further below with reference to FIG. 5a. In the illustrated example, the guide member 410 is upwardly biased by springs 418 and 419, and vertical movement of the guide member 410 is effected by sliding a knob 417 on the top of the apparatus back and forth, and the knob 417 has an angled member 416 on the bottom thereof that engages another angled member 415 on the top of the guide member 410. The guide member 410 may be moved up and down by other mechanisms in other embodiments, such as for example one or more levers, rotatable knobs, or other means.

Figure 5A:
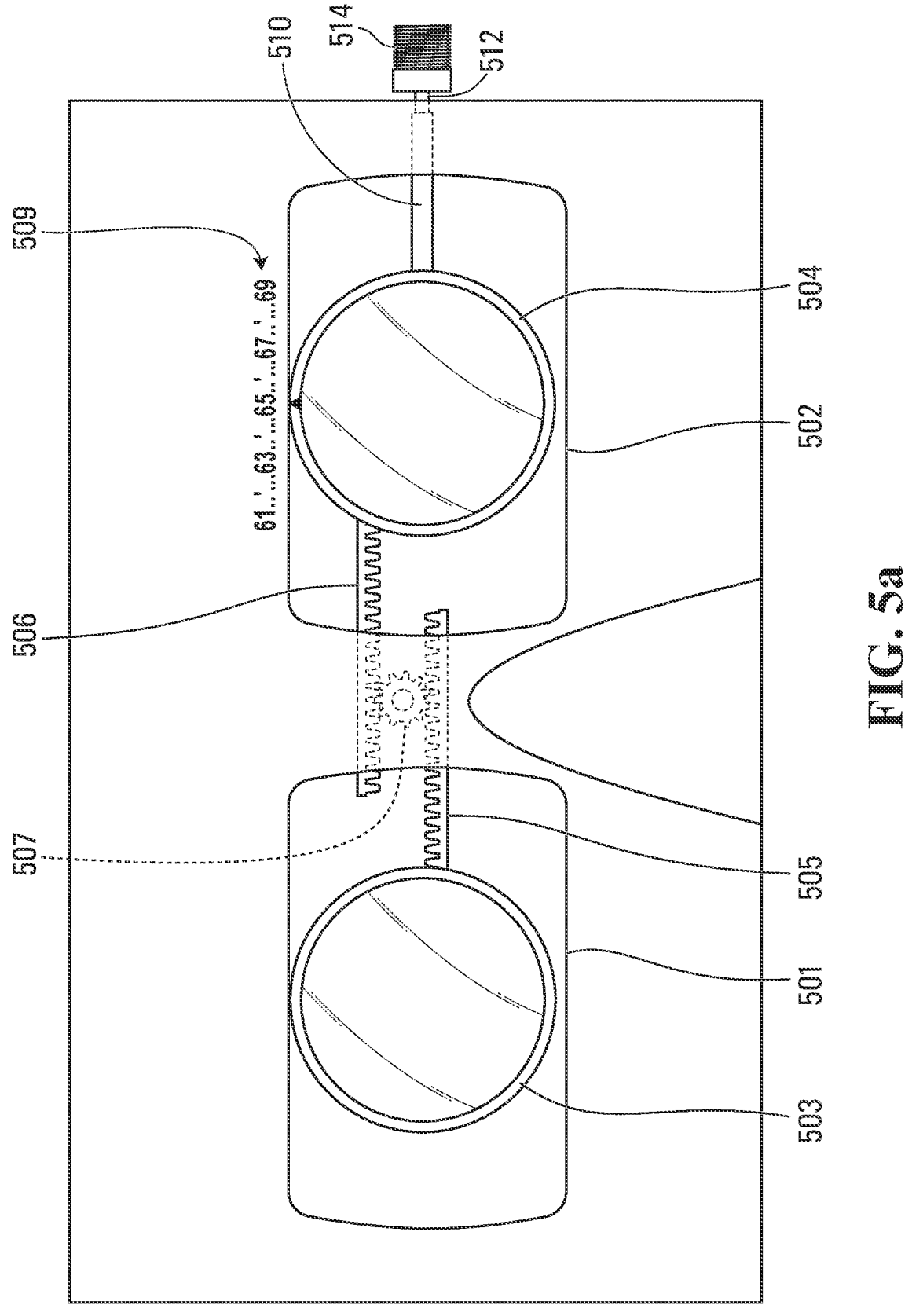
FIG. 5a shows another example IPD adjustment mechanism according to some embodiments of the present disclosure.
Figure 5B:
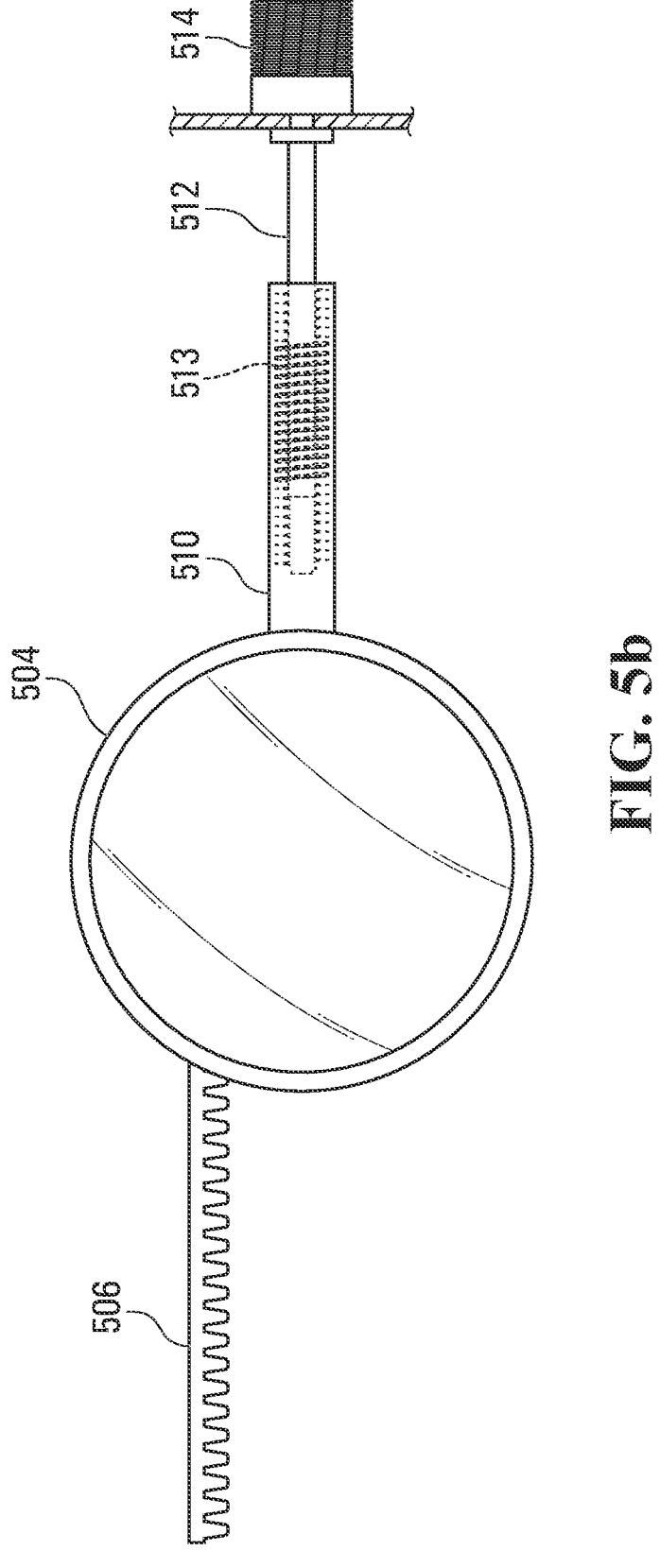

FIG. 5a shows an example IPD adjustment mechanism 500 according to some embodiments of the present disclosure. In the illustrated example, the IPD adjustment mechanism 500 comprises a rack and pinion-type mechanism. Similar to the example of FIG. 4, in the FIG. 5 example the body includes openings 501 and 502 for slidably receiving lenses 503 and 504 (which have frames in the FIG. 5 example) such that each lens 503/504 is laterally movable within its respective opening 501/502. Each lens 503/504 has a rack gear 506 extending inwardly therefrom, and the rack gears 506 engage a pinion gear 507 pivotally coupled to the body, such that movement of one of the lenses 503/504 towards the pinion gear 507 causes the other of the lenses 503/504 to move towards the pinion gear 507, and vice versa. A post 510 extends laterally outwardly from lens 504, and as best seen in FIG. 5b the post 510 is configured to receive a worm gear 513 mounted on a shaft 512 connected to an adjustment knob 514 extending out the side of the eye examination apparatus, such that when the knob 514 is rotated the lenses 503 and 504 move farther apart or closer together, depending on the direction the knob 514 is rotated. In the illustrated example, a scale 509 is printed on the body just above opening 502 to indicate the distance between the centers of the lenses 503 and 504, and the frame of lens 504 has a pointer/indicator mark thereon to indicate the position on the scale 509. As one of skill in the art will appreciate, since in the FIG. 5 example both lenses 503 and 504 move simultaneously, the markings on the scale 509 are calibrated appropriately (i.e. the 65 mm marking and the 67 mm marking of scale 509 are actually only 1 mm apart).

Figure 6A:
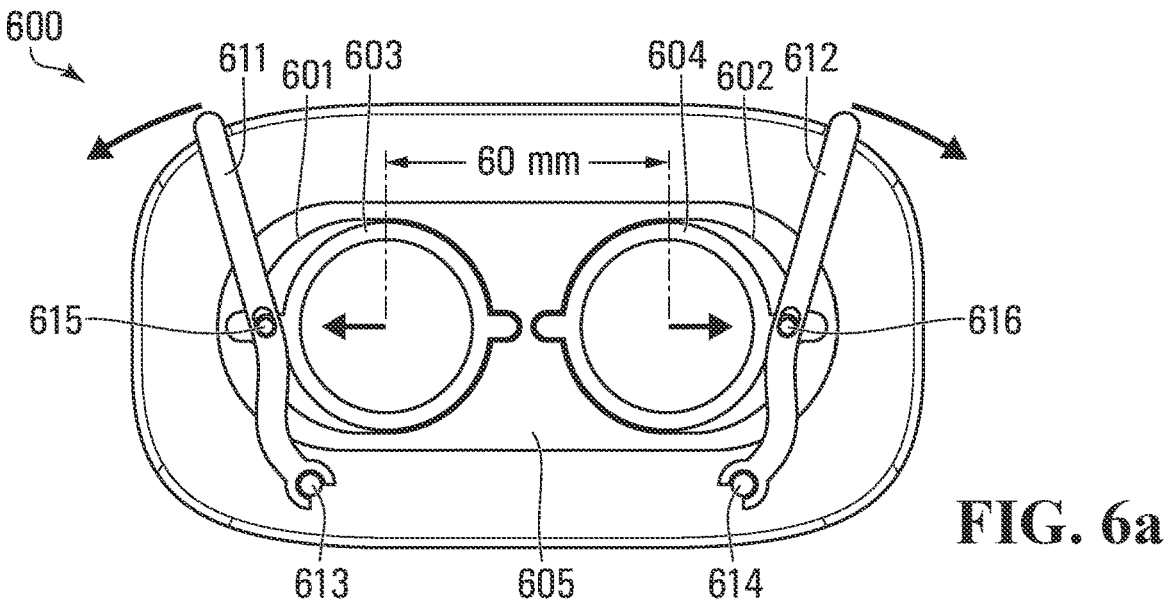
FIGS. 6a-6c show another example IPD adjustment mechanism according to some embodiments of the present disclosure.
Figure 6B:
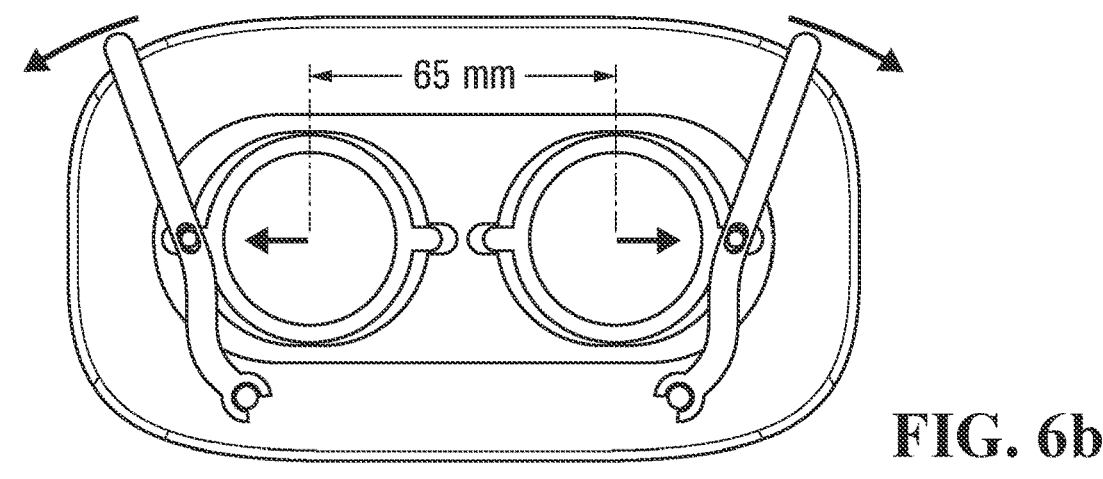
Figure 6C:
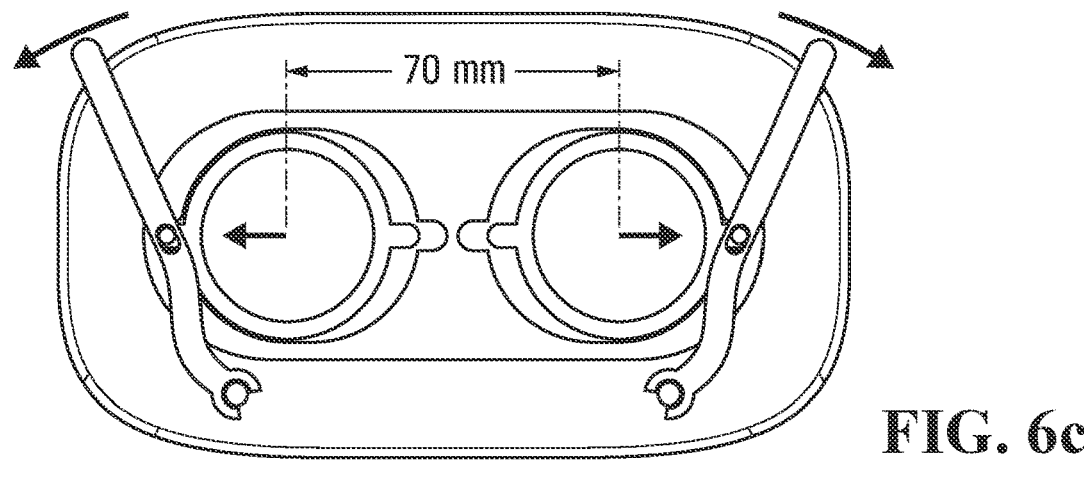

FIGS. 6a-6c show an example IPD adjustment mechanism 600 according to some embodiments of the present disclosure. In the illustrated example, the IPD adjustment mechanism 600 comprises a lever-actuated mechanism. Similar to the examples of FIGS. 4 and 5, in the FIG. 6a-6c example the body includes openings 601 and 602 for slidably receiving lenses 603 and 604 (which have frames in the example of FIGS. 6a-6c) such that each lens 603/604 is laterally movable within its respective opening 601/602. In the illustrated example, a pair of levers 611 and 612 are pivotally mounted on the body at their bottom ends, and each lever 611/612 is coupled to a pivot point 615/616 on a respective lens 603/604. In some implementations, a scale (not shown in FIGS. 6a-6c) may be printed on the body next to each of the openings 601 and 602 to indicate the distance from the center of the respective lenses 603 and 604 and a centreline between the openings (in the Example of FIGS. 6a-c, since each lens is separately adjustable, a user can determine the IPD by adding up the distances indicated on the scales above the two openings 601 and 602).

Figure 7:
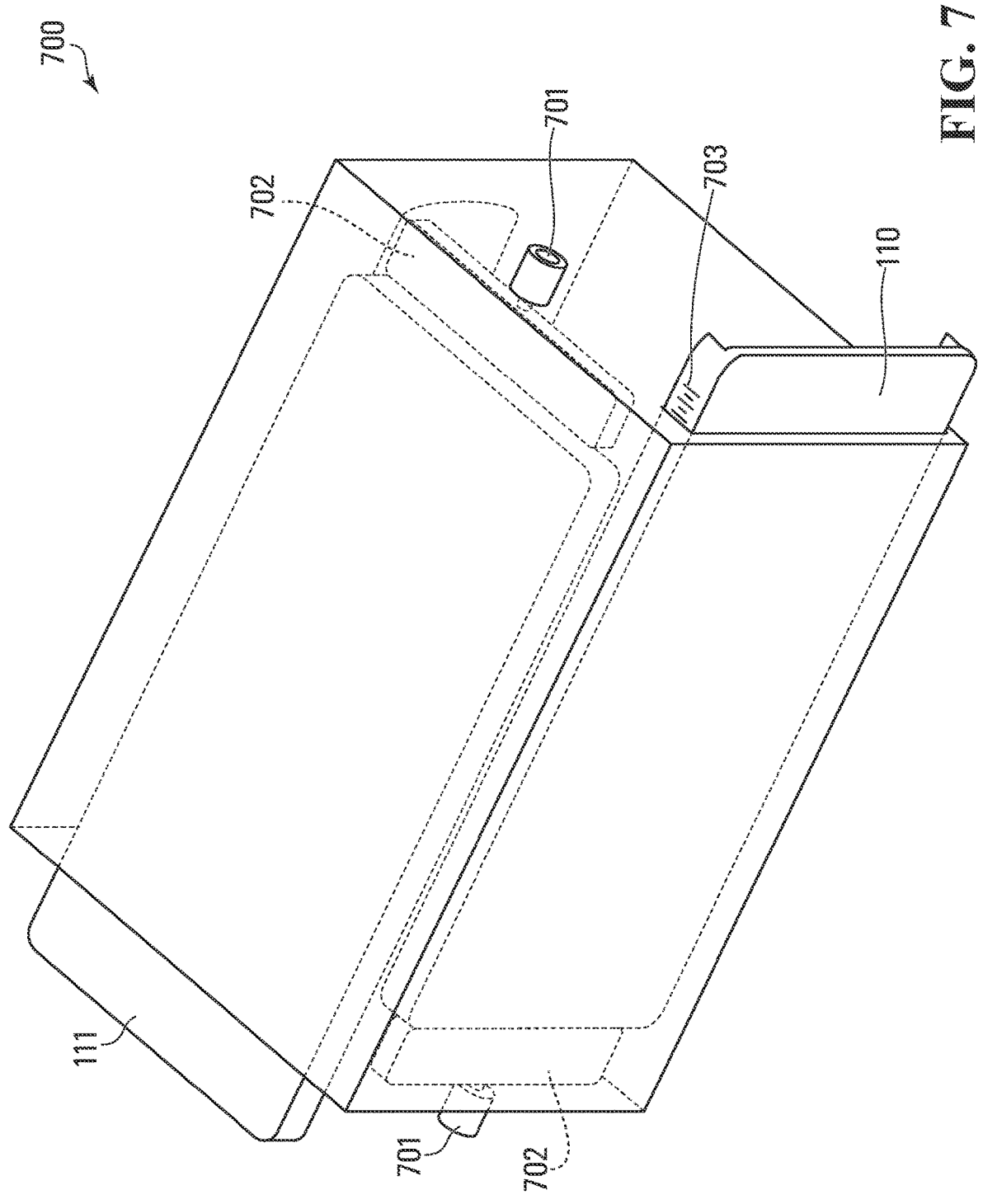
FIG. 7 shows an example cartridge adjustment mechanism according to some embodiments of the present disclosure.
Figure 8:
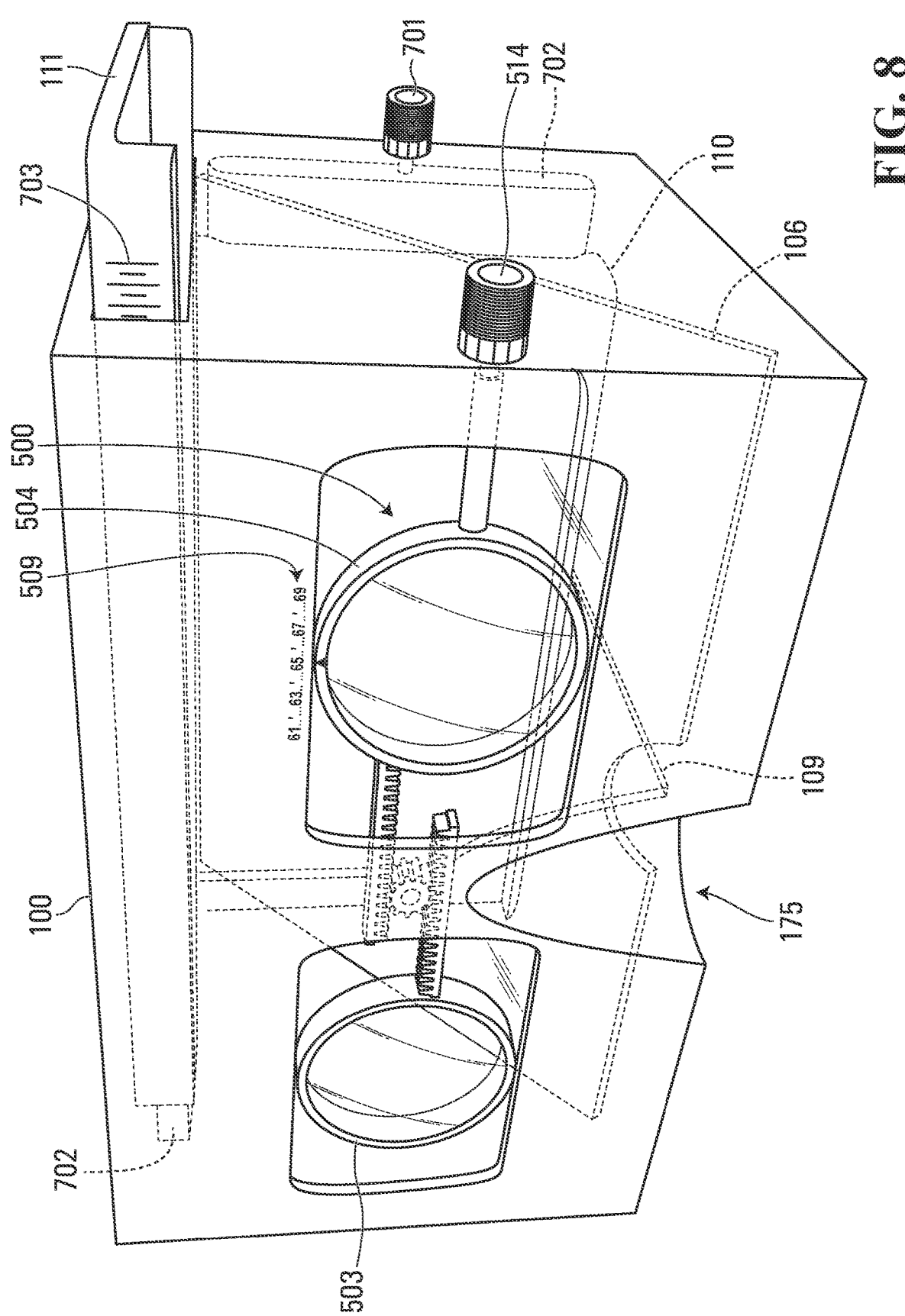
FIG. 8 shows an example eye examination apparatus incorporating the IPD adjustment mechanism of FIG. 5a and the cartridge adjustment mechanism of FIG. 7.

In some implementations of an eye examination apparatus that includes an IPD adjustment mechanism (e.g. any of mechanisms 400, 500 or 600 discussed above), the eye examination apparatus also include a complementary mechanism for adjusting the positions of the front and upper cartridges 110 and 111 that hold the smartphones/portable electronic devices. For example, FIG. 7 shows a cartridge adjustment mechanism 700 comprising, for each of the front and upper cartridges, a cartridge adjustment knob 701 that is operable to adjust the position of a cartridge stop 702. Each of the front and upper cartridges 110 and 111 may also have a scale 703 thereon, which indicates the position that cartridge should be in relation to the body for a given IPD. FIG. 8 shows an example eye examination apparatus having the IPD adjustment mechanism 500 of FIG. 5a and the cartridge adjustment mechanism 700 of FIG. 7, although it is to be understood that the cartridge adjustment mechanism 700 of FIG. 7 could also be included in an eye examination apparatus having the IPD adjustment mechanism 400 of FIG. 4 or the IPD adjustment mechanism 600 of FIGS. 6a-6c.

EXAMPLE APPLICATIONS

The eye examination apparatuses 100, 200 and 300 described herein have various applications as explained below. While many of these applications are described below in relation to the "smartphone embodiment" (i.e. the eye examination apparatus 100 depicted and described with reference to FIGS. 1a to 1p), it is to be understood that they can similarly be used in relation with the "professional embodiments" (i.e. the eye examination apparatus 200 depicted and described with reference to FIGS. 2a to 2l and/or the eye examination apparatus 300 depicted and described with reference to FIGS. 3a to 3c). Other applications maybe possible.

Visual Acuity: A specifically designed mobile application can enable the eye examination apparatus and the primary and secondary DCSs to precisely define the visual acuity of the users using one of the well-established, reliable and currently used eye testing systems i.e. HOTV. The application can provide instructions to the patient via verbal and/or written instructions and upon confirmation provided by the user, it can prompt the user to put a primary and optionally a secondary DCS (smartphone) into their respective cartridge slots of the eye examination apparatus 100. A default test begins by testing the right eye unless the right eye is non-functional or chosen otherwise by the user or the examiner (optometrist/physician). Random selection of H, O, T or V letters with sizes equivalent to 20/50 on Snellen's chart letters can be shown at a center of the display with a predetermined size reference letters at four sides. The user can then be prompted to respond if they recognize the letters and provide feedback in form of an eye or head movement toward the correct reference letter, vocal response or touch-screen input. Upon correct answers for three consecutive presentations, the size of the letters can be reduced, and the test can repeat itself. Alternatively, the size of the letters can increase after two consecutive wrong answers in the first set of presentations. As the user recognizes the letters and correctly spots them on the screen, the size of the target letters can be reduced. This process can continue until the user fails to provide three correct answers. A last letter size that the user is able to recognize reliably can be considered as their visual acuity. The cameras of the primary and secondary DCSs track the eyes during the visual acuity testing to ensure that the user gazed at the target.

Visual Field: The application, the eye examination apparatus, along with the primary and secondary DCSs, are also useful for performing automated visual field testing i.e. automated perimetry analysis. The patients or the examiners can determine a density and a span of a peripheral visual field to test. They can either choose to test a narrow span of the visual field (i.e. around the center of the vision) with high density test targets or a larger span of visual field with a variable density of test targets. Using a statistical model, brightness and locations of target lights can be randomly determined and the test gradually becomes harder/complex until a defined brightness/contrast threshold is reached at any tested peripheral target points. This analysis allows diagnosis of various neurological diseases based on the unique patterns of visual loss, for example, the inferior nasal visual field loss in glaucoma. Capturing and studying the pattern of visual loss can help the artificial intelligence and the examiner/physician to improve speed and precision of diagnosis. Results obtained can be conveniently stored in a secure system for further analysis and follow-up.

Color Vision: The eye examination apparatus can be employed to perform a standard color deficiency test. Numbers with different colors are shown to the patient and patient's feedback is collected and analyzed to detect different types of color blindness.

Amsler Grid: Amsler grid test is a screening test used to detect signs of diseases that damage retina or the optic nerve. Some examples of these conditions include Age Related Macular Degeneration, retinal detachment and optic neuritis all of which can lead to permanent blindness if not treated. Early detection and intervention are crucial in successful treatment of these conditions which emphasize the importance of screening tests in detection and management of these potentially disabling conditions. A grid of black lines spanning 20-30 degrees of the central field of vision is shown to each eye and the patient is asked to report any imperfection or distortion in the grid lines. Presence of imperfections prompts the physician to perform more thorough examinations leading to early diagnosis and treatment of the above-mentioned conditions.

Eye tracking: The cameras of the primary and secondary DCSs and the application are equipped with eye-tracking features. This is especially useful for detection and analysis of conditions that affect eye movement such as concussion, multiple sclerosis, traumatic brain injury, and neurodegenerative brain diseases (for example, Alzheimer's disease, Parkinson's disease, Fronto-Temporal Dementia. Using the eye-tracking feature, the eye examination apparatus can examine patients' eye movements while performing tasks such as self-paced saccades or smooth pursuit to further analyze the course of the disease and assess the effectiveness of the treatments.

With advancement in smartphone and mobile technology, display resolution and camera resolution continue to improve which can improve visual acuity testing and other eye measurements by the eye examination apparatus.

Various other applications of the eye examination apparatus include observation and analysis of:

afferent and efferent visual functions;

static eye features: eyelids, eyelid fissures, irises, pupil shape and size, pupil color and sclera.

dynamic eye features: blinking, opening and closure of the eyes, pupil changes to light and near/far vision, regularity of the pupil reactions, and various eye movements, testing the dry eye syndrome (or equivalent eye abnormalities e.g. computer-eye syndrome etc.)

testing the refraction of the eyes to define the prescription of glasses;

optic nerve, retina and their vascular features; and refraction measurement for other purposes.

Further, the eye examination apparatus can be employed to perform a variety of routine eye examinations to diagnose and assess common to severe eye conditions, a few of which are explained briefly hereunder.

Afferent Visual System (AVS)

AVS is related to all visual and brain functions that are responsible for capturing the images from the environment and analyzing them in order to create visual perceptions. AVS is measured through different visual attributes including visual acuity, visual field, color vision, stereovision, depth perception, pupil size/shape in reaction to light and/or distance, and the integrity of peripheral vision such as Amsler grid test.

Visual acuity: Visual acuity test is a measure of visual clarity at the center of vision (occasionally visual acuity is measured at peripheral vision as well). The clarity of vision is compared to the average visual clarity in the normal population which is called visual acuity. Different methods at different distances are used to test visual acuity, such as E-Chart, stylized letters, Landolt rings, pediatric symbols, or symbols for the illiterate. The standard measure of reporting normal visual acuity are 6/6 or 20/20, in Europe and North America, respectively. 20/20 or 6/6 vision means that the observer can clearly see a target at 20 feet (or 6 meters) (representing the nominator) as can a person with average normal vision (represented by denominator). However, if someone has reduced vision, for example 6/12 or 20/40, it means that the person can see a target clearly at 6 meters (20 feet) whereas an individual with average normal vision can see the same size object at 12 meters (40 feet).

Traditionally with E-chart visual acuity testing the size of the letter that needs to be seen clearly to represent 20/20 vision was determined to be 5 arc minutes (1 arc minute is $\frac{1}{60}$ of a degree of visual angle). The letter E has 3 sequences of dark and bright lines that need to be distinguished before the observer can clearly recognize the letter and its direction. More recently, the HOTV method of visual acuity testing has become a standard test. The HOTV system contains the letters (H, O, T, and V) which involves distinction of 3 repetition of light and bright pixels before the letter is distinguished. Therefore, vision with clarity of recognizing an image at 1.6 arc minute (the letters representing 20/20 vision) can recognize HOVT letters. As such the majority of commercially available cellphones since 2012 (over 70 cellphone models-see cellphone table) can provide close or above 37.5 PPD (pixel per degree) (representing 1.6 arc minute at Eye examination apparatus resolution and can be used to test 20/20 vision with HOTV system).

Visual field and peripheral vision: Peripheral vision is a fundamental part of vision that provides awareness of the environment that can prevent accidents, collisions with objects approaching from the corners of the vision, etc.

Measuring the visual field can be performed during an eye examination by a physician i.e. confrontation visual field test, which is neither sensitive nor specific. Alternatively, visual field testing can be done automatically by a physician or optometrist most commonly at a doctor office where the individual sits in front the machine and fixates at the center of the visual field; depending on the model of the visual field test machine the visual stimuli either is moved or flashed manually or by the machine at different areas of the visual field; visual stimulation is usually a dot of light. The patient responds to seeing the light by notifying the examiner or clicking a button. Sophisticated automatic visual tests use statistical models to increase the reliability as well as reduce the duration of the tests. These tests can now be performed virtually using the eye examination apparatus.

Color vision: Color vision is defined as the ability of visual system to discriminate between different wavelengths of light within visible light spectrum regardless of its intensity[1]. Humans are able to see colors due to the presence of cone retinal photoreceptors. Their peak sensitivity varies in three ranges of short (~535 nm) medium (~565 nm) and long (~440 nm) wavelengths. Hence, they are called S, M and L photoreceptors[2]. Color blindness is a condition in which colors are not perceived properly. It can happen due to loss of cones (dichromacy), changes in spectral sensitivity of cones (anomalous trichromacy) or damage to the optic nerve or visual cortex. These could happen genetically or due to diseases or toxin-induced insults to the retinal, optic nerve or cortical cells[3].

[1] DeValois K, Webster M. Color vision. Scholarpedia. 2011; 6(4):3073.

[2] DeValois K, Webster M. Color vision. Scholarpedia. 2011; 6(4):3073.

[3] DeValois K, Webster M. Color vision. Scholarpedia. 2011; 6(4):3073.

Stereovision, depth perception and stereoscopic display: Stereoscopic display, also called 3D display or head-mounted display (HMD) comprises a visual display e.g. LCD or LED display, in front of each eye that works based on the principle of stereopsis[4]. It operates by showing slightly different 2D perspectives of the same object to each eye. The minor deviation of the object between the images is precisely equal to the natural perspective of the binocular vision. This deviation creates an illusion of a 3D environment[5] and helps vision in its depth perception.

[4] Woods A J. Crosstalk in stereoscopic displays: a review. J Electron Imaging. 2012 Dec. 5; 21(4):040902.

[5] Woods A J. Crosstalk in stereoscopic displays: a review. J Electron Imaging. 2012 Dec. 5; 21(4):040902.

Pupillary response: Pupils respond to near/far objects and light by contraction and relaxation. These are called near/light pupil response. In the near response, pupils contract because the human lens naturally distorts light near its periphery. Pupils naturally constrict in near object vision to avoid this distortion and enhance visual clarity[6]. Pupils constrict in response to bright light to reduce the amount of light entering the eye.

[6] Pupillary reflex—Wikipedia. McGraw-Hill; 2012

Efferent Visual System (EVS)

Efferent visual system (EVS) functions relate to all visual and brain functions that are related to eye movements, reflexes and alignment. EVS assessment includes measuring eye alignment/misalignment, saccadic/pursuit eye movements and the eye movement components. These components include saccade amplitude, accuracy, maximum speed, and number of saccades in self-paced, memory-based and reflexive (i.e. visually targeted) saccades. Moreover, EVS measurements include abnormal eye movements such as nystagmus/oscillation/intrusions of the eye at neutral or different gaze positions, and eye reflexes such as vestibulo-ocular-reflex (VOR) and inhibition (VOI).

Pursuit eye movement: Smooth pursuit eye movements are slower than saccades and evolved to fixate on a moving object at the center of vision i.e. when the image is fallen on the fovea[7]. This movement is under voluntary control. However, in the absence of an object only highly trained individuals are able to make smooth pursuits eye movements and most of the people will simply perform saccades[8]. Smooth pursuit is highly controlled by the brain (frontal eye field in the frontal lobe).

[7] Purves D, Augustine G J, Fitzpatrick D, Katz L C, LaMantia A-S, McNamara J O, et al. Types of Eye Movements and Their Functions. 2001.

[8] Purves D, Augustine G J, Fitzpatrick D, Katz L C, LaMantia A-S, McNamara J O, et al. Types of Eye Movements and Their Functions. 2001.

Saccade: A saccade is defined as a synchronous and rapid movement of the eyes between two points[9]. In comparison to VOR response that is controlled by a relatively straight-forward pathways, saccadic response is driven by complex and polysynaptic pathways that originate from the frontal eye field (FEF) cerebellum, or superior colliculus[10].

[9] Takahashi M, Shinoda Y. Brain Stem Neural Circuits of Horizontal and Vertical Saccade Systems and their Frame of Reference. Neuroscience. 2018 Nov. 10; 392:281-328.

[10] Termsarasab P, Thammongkolchai T, Rucker J C, Frucht S J. The diagnostic value of saccades in movement disorder patients: a practical guide and review. J Clin Mov Disord. 2015 Oct. 15; 2:14.

Self-paced Saccade: Self-paced saccade (SPSs) is defined as a voluntary saccade between two fixed targets. The anterior cingulate cortex is responsible for maintaining the motivation to perform the task. The FEF, prefrontal cortex (dorsolateral part) and superior colliculus of the midbrain constitute the pathways that govern self-paced saccades[11,12]. More precisely, to generate a horizontal saccade initiation, signals from the FEFs are sent to paramedian reticular formation in pons to activate cranial nerve 6 nucleus. Further, the signal will continue to go to midbrain from Medial Longitudinal Fasciculus (MLF) to activate cranial nerve 3 nucleus. These 2 cranial nuclei are fundamentally responsible for horizontal eye movements. The vertical saccade is generated by initiation signals from FEFs transmitted to the rostral interstitial nuclei of MLF, 3ed and 4th cranial nerves[13,14] which in turn generate and control vertical eye movements.

[11] Heitger M H, Anderson T J, Jones R D, Dalrymple-Alford J C, Frampton C M, Ardagh M W. Eye movement and visuomotor arm movement deficits following mild closed head injury. Brain. 2004 March; 127(Pt 3):575-90.

[12] Heitger M H, Jones R D, Macleod A D, Snell D L, Frampton C M, Anderson T J. Impaired eye movements in post-concussion syndrome indicate suboptimal brain function beyond the influence of depression, malingering or intellectual ability. Brain. 2009 October; 132(Pt 10):2850-70.

[13] Williams I M, Ponsford J L, Gibson K L, Mulhall L E, Curran C A, Abel L A. Cerebral control of saccades and neuropsychological test results after head injury. J Clin Neurosci. 1997 April; 4(2):186-96.

[14] Heitger M H, Anderson T J, Jones R D, Dalrymple-Alford J C, Frampton C M, Ardagh M W. Eye movement and visuomotor arm movement deficits following mild closed head injury. Brain. 2004 March; 127(Pt 3):575-90.

Studies on mTBI patients have revealed impairments of several characteristics of horizontal SPSs such as total number of saccades and intersaccadic intervals[15]. Patients with mTBI performed fewer SPSs with a significantly increased intersaccadic interval which indicates impairment of the prefrontal function[16,17]. In addition to the parameters mentioned above, other parameters such as saccadic velocity to accuracy ratio (S/A ratio) and saccade gain are among common metrics to evaluate horizontal saccadic performance[18,19]. Studies have also demonstrated impairment in vertical saccadic performance such as efficiency, amplitude, peak, acceleration and position errors following mTBI[20].

[15] Taghdiri F, Chung J, Irwin S, Multani N, Tarazi A, Ebraheem A, et al. Decreased Number of Self-Paced Saccades in Post-Concussion Syndrome Associated with Higher Symptom Burden and Reduced White Matter Integrity. J Neurotrauma. 2018 Mar. 1; 35(5):719-29.

[16] Taghdiri F, Chung J, Irwin S, Multani N, Tarazi A, Ebraheem A, et al. Decreased Number of Self-Paced Saccades in Post-Concussion Syndrome Associated with Higher Symptom Burden and Reduced White Matter Integrity. J Neurotrauma. 2018 Mar. 1; 35(5):719-29.

[17] Heitger M H, Jones R D, Macleod A D, Snell D L, Frampton C M, Anderson T J. Impaired eye movements in post-concussion syndrome indicate suboptimal brain function beyond the influence of depression, malingering or intellectual ability. Brain. 2009 October; 132(Pt 10):2850-70.

[18] Hunfalvay M, Roberts C-M, Murray N, Tyagi A, Kelly H, Bolte T. Horizontal and vertical self-paced saccades as a diagnostic marker of traumatic brain injury. Concussion. 2019 Jul. 25; 4(1):CNC60.

[19] Cifu D X, Wares J R, Hoke K W, Wetzel P A, Gitchel G, Carne W. Differential eye movements in mild traumatic brain injury versus normal controls. J Head Trauma Rehabil. 2015 February; 30(1):21-8.

[20] Hunfalvay M, Roberts C-M, Murray N, Tyagi A, Kelly H, Bolte T. Horizontal and vertical self-paced saccades as a diagnostic marker of traumatic brain injury. Concussion. 2019 Jul. 25; 4(1):CNC60.

Reflexive (visual targets) saccades: Reflexive saccades are defined in relation to voluntary saccades. While the latter involve voluntarily controlled cognitive processes, reflexive saccades occur in response to the appearance of a new target eccentric to the point of fixation[21].

[21] Walker J. Human saccadic eye movements. Scholarpedia. 2012; 7(7):5095.

Memory based saccade: Memory-guided saccade is defined as a saccade to the place of a target that flashed briefly. This involves remembering the location of the briefly visible target. A defect in the basal ganglia or frontal lobes where working memory is processed, results in memory guided saccade dysfunction[22].

[22] Walker J. Human saccadic eye movements. Scholarpedia. 2012; 7(7):5095.

Saccade velocity: Most frequently measured velocity parameter is peak saccade velocity. It is defined as the maximum speed of the eyes during a saccade. The typical peak velocity of saccades in a normal person ranges from 30 to 700 degrees/s with an amplitude between 0.5 to 40 degrees[23]. Changes in peak saccade velocity could be a viable indicator of psychophysiological arousal (sympathetic nervous system activation), mental activity workload or prediction of the subsequent fixation point value[24,25,26].

[23] Wong A M F. Eye Movements; Saccades. Encyclopedia of the neurological sciences. Elsevier; 2014. p. 249-51.

[24] Di Stasi L L, Catena A, Cañas J J, Macknik S L, Martinez-Conde S. Saccadic velocity as an arousal index in naturalistic tasks. Neurosci Biobehav Rev. 2013 June; 37(5):968-75.

[25] Brunyé T T, Drew T, Weaver D L, Elmore J G. A review of eye tracking for understanding and improving diagnostic interpretation. Cogn Research. 2019 Feb. 22; 4(1):7.

[26] Xu-Wilson M, Zee D S, Shadmehr R. The intrinsic value of visual information affects saccade velocities. Exp Brain Res. 2009 July; 196(4):475-81.

Time to peak velocity: As previously described, saccadic peak velocity is defined as the maximum velocity reached during a saccade. The time spent between the beginning of the saccade until reaching the peak of velocity is called time to peak velocity.

Saccade accuracy, latency and amplitude: Saccade accuracy is the accuracy with which a saccade fixates a target on the center of fovea. Average landing error and average landing variability are two parameters that are used to measure accuracy and precision of the saccades respectively[27]. Studies have shown that even small saccades (between 14 to 20 degrees) are accurate enough to precisely center the stimulus on the fovea[28]. Studies have demonstrated alterations in saccadic accuracy following mild traumatic brain injury[29]. This indicates the potential of these parameters for the diagnosis and follow up of the patient suffering from mTBI.

[27] Poletti M, Intoy J, Rucci M. Accuracy and precision of small saccades. Sci Rep. 2020 Sep. 30; 10(1):16097

[28] Poletti M, Intoy J, Rucci M. Accuracy and precision of small saccades. Sci Rep. 2020 Sep. 30; 10(1):16097.

[29] Heitger M H, Jones R D, Macleod A D, Snell D L, Frampton C M, Anderson T J. Impaired eye movements in post-concussion syndrome indicate suboptimal brain function beyond the influence of depression, malingering or intellectual ability. Brain. 2009 October; 132(Pt 10):2850-70.

Saccade gain: Saccade gain is calculated based on the saccade amplitude and is a parameter that is used to measure saccade accuracy. This parameter defines if the saccade is hypo- or hypermetric and calculated by dividing the actual saccade amplitude by desired saccade amplitude[30].

[30] Knox Paul, "The parameters of eye movement", accessed 2020 December, www.docenti.unina.it/webdocenti-be/allegati/materiale-didattico/412703

Position error. Is a parameter to measure the motor accuracy of saccades. It is closely related to saccade gain. The mean absolute position error measures the difference between desired and actual eye position. However, saccade amplitude clarifies the direction of that error by showing weather there was a hypo- or hypermetria. These parameters are effective means of measuring the impact of TBI on saccadic eye movements[31]. "Mean absolute position error of the final eye position [PEreflexive=|(EPfin−SP)/SP|×100], gain of the primary saccade (Gp=EPprim/SP) and gain of the final eye position (Gf=EPfin/SP), where EPprim is the eye position after the initial saccade, EPfin is the final eye position and SP is the stimulus position"[32].

[31] Heitger M H, Anderson T J, Jones R D, Dalrymple-Alford J C, Frampton C M, Ardagh M W. Eye movement and visuomotor arm movement deficits following mild closed head injury. Brain. 2004 March; 127(Pt 3):575-90.

[32] Heitger M H, Anderson T J, Jones R D, Dalrymple-Alford J C, Frampton C M, Ardagh M W. Eye movement and visuomotor arm movement deficits following mild closed head injury. Brain. 2004 March; 127(Pt 3):575-90.

Saccadic intrusions: Saccadic intrusions are defined as saccades that interrupt fixation. They happen irregularly and categorized based on whether or not they are separated by a brief interval of fixation. Some examples of the saccades that possess an intersaccadic interval include square wave jerks, macro-saccadic oscillations and macro square wave jerks. Among those that happen as back-to-back saccades without any intersaccadic interval, are opsoclonus, voluntary nystagmus and ocular flutter[33]. While saccadic intrusions could be found in normal individuals, they could also indicate underlying disorders/dysfunction of brainstem, cerebellum, superior colliculus, basal ganglia or cerebellum.

[33] Lemos J, Eggenberger E. Saccadic intrusions: review and update. Curr Opin Neurol. 2013 February; 26(1):59-66.

Vestibulo-ocular reflex and inhibition: Vestibulo-ocular reflex (VOR) is a 3-dimensional reflex governed by the inner ear vestibular system and involves cranial nerves III, IV, VI, VIII, their respective nuclei, as well as medial longitudinal fasciculus (MLF) to maintain visual stability during head movement. VOR stabilizes gaze by moving the eye to the opposite direction from the head movement. A defect in the vestibular system, the associated nuclei or their interconnecting pathways could lead to a dysfunctional VOR[34]. Conversely, the Vestibulo-ocular inhibition (VOI) demonstrates the ability of the EVS to inhibit VOR when the head follows a moving object by rotating the whole body and keeping the eye stationary and fixated on the target.

[34] Halmagyi G M, Chen L, MacDougall H G, Weber K P, McGarvie L A, Curthoys I S. The video head impulse test. Front Neurol. 2017 Jun. 9; 8:258.

Dynamic visual acuity: Maintaining visual acuity during head movement (dynamic visual acuity) is the outcome of an interplay between vestibular, visuomotor and visual systems[35]. Normally, there is a certain degree of reduction in visual acuity during movement. Reduction of visual acuity during movement beyond its normal range (oscillopsia) indicates a non-compensated insult to the pathways responsible for VOR[36]. Recent studies have established a relationship between recovery of dynamic visual acuity parameters and improvement of post-concussion syndrome[37].

[35] Landers M R, Donatelli R, Nash J, Bascharon R. Evidence of dynamic visual acuity impairment in asymptomatic mixed martial arts fighters. Concussion. 2017 November; 2(3):CNC41.

[36] Landers M R, Donatelli R, Nash J, Bascharon R. Evidence of dynamic visual acuity impairment in asymptomatic mixed martial arts fighters. Concussion. 2017 November; 2(3):CNC41.

[37] Landers M R, Donatelli R, Nash J, Bascharon R. Evidence of dynamic visual acuity impairment in asymptomatic mixed martial arts fighters. Concussion. 2017 November; 2(3):CNC41.

Nystagmus: Nystagmus is defined as involuntary eye movement in a horizontal, vertical or rotatory fashion. Based on movement speed, two types of nystagmus could be distinguished from each other[38]. Pendular nystagmus is a type that consists of slow sinusoidal oscillations in both phases while Jerk nystagmus is characterized by a slow drift and a rapid corrective saccade[39].

[38] Leigh R J, Zee D S. The neurology of eye movements. Oxford University Press; 2015.

[39] Leigh R J, Zee D S. The neurology of eye movements. Oxford University Press; 2015.

Proper characterization of nystagmus helps with the diagnosis of causative defects and pathologies. The first step in finding the cause of the nystagmus is to determine the effect of removing the fixation on the severity of the nystagmus. As an example, increasing the severity of nystagmus after removing fixation indicates a peripheral origin[40]. A peripheral nystagmus that is caused by a peripheral vestibular pathology usually causes a jerk nystagmus that beats away from the side of the lesion. In contrast, a congenital nystagmus is usually horizontal and accentuated by fixation as well as anxiety[41]. Moreover, presence of a purely torsional or vertical jerk nystagmus while the eyes are at a near center position mainly indicates a central lesion involving the vestibular pathways[42].

[40] Serra A, Leigh R J. Diagnostic value of nystagmus: spontaneous and induced ocular oscillations. J Neurol Neurosurg Psychiatr. 2002 December; 73(6):615-8.

[41] Serra A, Leigh R J. Diagnostic value of nystagmus: spontaneous and induced ocular oscillations. J Neurol Neurosurg Psychiatr. 2002 December; 73(6):615-8.

[42] Serra A, Leigh R J. Diagnostic value of nystagmus: spontaneous and induced ocular oscillations. J Neurol Neurosurg Psychiatr. 2002 December; 73(6):615-8.

Structure of the Visual System

The measurements include (1) optic nerve thickness and shape, (b) retina/macula layers, thickness and shape and (3) vascular structure and live function and reaction of the vessels to different maneuvers for example Valsalva or fast breathing or visual stimulation such as stationary vs motion pictures. Ocular coherence tomography technology will be placed at the display and cameras which can demonstrate microstructure of the optic nerve, retina and their vessels.

Virtual Reality (VR)

A platform through which a computer generated 3D rendered environment is presented to the viewer using one or more stereoscopic displays combined with a plethora of novel technologies such as head and eye tracking sensors, software frameworks, development tools and input devices packaged in a head-mounted setup designed to create an illusion of reality. Input devices enable the user to interact with the virtual environment[43].

[43] Cipresso P, Giglioli I A C, Raya M A, Riva G. The past, present, and future of virtual and augmented reality research: A network and cluster analysis of the literature. Front Psychol. 2018 Nov. 6; 9:2086.

Eye Tracking

Eye tracking is an objective method of assessing ocular function. Eye tracking systems and softwares are designed to measure different aspects of ocular motor function including movement, position, latencies, frequency of moves, etc.[44]. It also measures the pattern of eye movements between the fixation points including saccade amplitude (in degrees), speed, number of saccades[45,46], etc. Position measures calculate the Cartesian coordinates of the gaze and latency measures quantify the duration of saccades and fixations (defined as pause at a spatial location for more than 99 milliseconds). Moreover, the quantity of saccades and number for fixations and blinks are among mostly studied frequency measures[47].

[44] Holmqvist K, Nyström M, Andersson R, Dewhurst R, Van de Weijer J. Eye Tracking: A Comprehensive Guide To Methods And Measures. 2011 Jan. 1.

[45] Liversedge S P, Findlay J M. Saccadic eye movements and cognition. Trends Cogn Sci (Regul Ed). 2000 January; 4(1):6-14

[46] Heitger M H, Jones R D, Macleod A D, Snell D L, Frampton C M, Anderson T J. Impaired eye movements in post-concussion syndrome indicate suboptimal brain function beyond the influence of depression, malingering or intellectual ability. Brain. 2009 October; 132(Pt 10):2850-70

[47] Brunyé T T, Drew T, Weaver D L, Elmore J G. A review of eye tracking for understanding and improving diagnostic interpretation. Cogn Research. 2019 Feb. 22; 4(1):7

A typical eye tracking setup consists of an infrared or semi-infrared light source, a camera and a software that processes the images and tracks the eye movement mainly through pupil tracking[48]. More sophisticated tracking systems include light emitters to produce light reflections on the eye surface. The relative position of the reflected points to the pupil will be used to calculate the eye position vectors and point of regard[49].

[48] Brunyé T T, Drew T, Weaver D L, Elmore J G. A review of eye tracking for understanding and improving diagnostic interpretation. Cogn Research. 2019 Feb. 22; 4(1):7.

[49] Hansen D W, Ji Q. In the eye of the beholder: a survey of models for eyes and gaze. IEEE Trans Pattern Anal Mach Intell. 2010 March; 32(3):478-500.

Diseases that the Eye Examination Apparatus can Help with Diagnosis and Monitoring Recovery Another disease that the eye examination apparatus can help with diagnosis and monitoring the recovery is Mild traumatic brain injury (mTBI). Proper eye movement relies extensively on the functional integrity of the brain and its pathways. Moreover, attention, response inhibition, memory, motor planning and speed of information processing play significant roles in the control of eye movements. Studies have established a significant correlation between mTBI and impairment of EVS[50]. Interestingly, the eye movement deficits happen independent of neuropsychological symptoms of mTBI[51]. Meta-analysis of studies focused on neuropsychological sequelae of mTBI demonstrated that neurocognitive determinants of the post-concussion syndrome completely resolve 1-3 months after the impact. Moreover, imaging entities have limited ability in detecting abnormalities in patients with post-concussion syndrome[52,53].

[50] Heitger M H, Jones R D, Macleod A D, Snell D L, Frampton C M, Anderson T J. Impaired eye movements in post-concussion syndrome indicate suboptimal brain function beyond the influence of depression, malingering or intellectual ability. Brain. 2009 October; 132(Pt 10):2850-70.

[51] Heitger M H, Anderson T J, Jones R D, Dalrymple-Alford J C, Frampton C M, Ardagh M W. Eye movement and visuomotor arm movement deficits following mild closed head injury. Brain. 2004 March; 127(Pt 3):575-90.

[52] Schretlen D J, Shapiro A M. A quantitative review of the effects of traumatic brain injury on cognitive functioning. Int Rev Psychiatry. 2003 November; 15(4):341-9.

[53] Heitger M H, Jones R D, Macleod A D, Snell D L, Frampton C M, Anderson T J. Impaired eye movements in post-concussion syndrome indicate suboptimal brain function beyond the influence of depression, malingering or The assessment of EVS and AVS abnormalities through the eye examination apparatus can prove useful in identifying many eye and brain disorders such as: a. Eye diseases such as macular degeneration, glaucoma, optic neuropathy, etc. (AVS abnormalities); b. Neurodegenerative diseases like Parkinson disease, Alzheimer disease, etc.; c. Psychiatric diseases such as schizophrenia, ADHD, etc. (AVS and EVS abnormalities); d. Common eye conditions such as amblyopia.

Supported Smartphones

There are many possibilities for the smartphones that can be used with the eye examination apparatus 100 described herein. The following is a non-exclusive list of smartphones which may be used with the eye examination apparatus 100. It is to be understood that additional smartphones, or other portable electronic devices with or without phone service may be compatible as well, so long as they include a suitable camera and display.

| Manufacturer and model name | Year introduced | Screen size | Screen area | Resolution | Ratio | PPI | PPD |
|---|---|---|---|---|---|---|---|
| Sony Xperia XZ Premium | 2017 | 5.46" | 12.74 square inches (4.8" × 2.7") | 3840 × 2160 UHD-1 | 16:09 | 806.93 | 65.7 |
| Sony Xperia Z5 Premium | 2015 | 5.5" | 12.93 square inches (4.8" × 2.7") | 3840 × 2160 UHD-1 | 16:09 | 801.06 | 65.2 |
| Samsung Galaxy S6 | 2015 | 5.1" | 11.11 square inches (4.4" × 2.5") | 2560 × 1440 QHD | 16:09 | 575.92 | 46.4 |
| Samsung Galaxy S6 Edge | 2015 | 5.1" | 11.11 square inches (4.4" × 2.5") | 2560 × 1440 QHD | 16:09 | 575.92 | 46.4 |
| Samsung Galaxy S7 | 2016 | 5.1" | 11.11 square inches (4.4" × 2.5") | 2560 × 1440 QHD | 16:09 | 575.92 | 46.4 |
| Samsung Galaxy S8 | 2017 | 5.8" | 13.23 square inches (5.2" × 2.5") | 2960 × 1440 | 37:18:00 | 567.53 | 47 |
| Samsung Galaxy S9 | 2018 | 5.8" | 13.23 square inches (5.2" × 2.5") | 2960 × 1440 | 37:18:00 | 567.53 | 47 |
| LG G6 | 2017 | 5.7" | 13 square inches (5.1" × 2.5") | 2880 × 1440 | 2:01 | 564.9 | 46.5 |
| Microsoft Lumia 950 | 2015 | 5.2" | 11.55 square inches (4.5" × 2.5") | 2560 × 1440 QHD | 16:09 | 564.85 | 45.6 |
| HTC 10 | 2016 | 5.2" | 11.55 square inches | 2560 × 1440 QHD | 16:09 | 564.85 | 45.6 |
| Motorola Droid Turbo | 2014 | 5.2" | 11.55 square inches (4.5" × 2.5") | 2560 × 1440 QHD | 16:09 | 564.85 | 45.6 |
| LG G7 ThinQ | 2018 | 6.1" | 14.16 square inches (5.5" × 2.6") | 3120 × 1440 | 13:06 | 563.32 | 45.9 |
| LG G5 | 2016 | 5.3" | 12 square inches (4.6" × 2.6") | 2560 × 1440 QHD | 16:09 | 554.19 | 44.9 |
| Samsung Galaxy S10 | 2019 | 6.1" | 14.4 square inches (5.5" × 2.6") | 3040 × 1440 | 19:09 | 551.44 | 46.1 |
| Samsung Galaxy Note Edge | 2014 | 5.6" | 14.09 square inches (4.7" × 3") | 2560 × 1600 WQXGA | 8:05 | 539.08 | 43.9 |
| Nokia 9 | 2019 | 5.99" | 14.35 square inches (5.4" × 2.7") | 2880 × 1440 | 2:01 | 537.55 | 44.7 |
| Huawei Mate 20 Pro | 2018 | 6.4" | 15.58 square inches (5.8" × 2.7") | 3120 × 1440 | 13:06 | 536.92 | 45.4 |
| LG V40 ThinQ | 2018 | 6.4" | 15.58 square inches (5.8" × 2.7") | 3120 × 1440 | 13:06 | 536.92 | 45.4 |
| LG V30 | 2017 | 6" | 14.4 square inches (5.4" × 2.7") | 2880 × 1440 | 2:01 | 536.66 | 44.6 |
| LG G3 | 2014 | 5.5" | 12.93 square inches (4.8" × 2.7") | 2560 × 1440 QHD | 16:09 | 534.04 | 41.9 |
| Oppo Find 7 | 2014 | 5.5" | 12.93 square inches (4.8" × 2.7") | 2560 × 1440 QHD | 16:09 | 534.04 | 41.9 |
| LG G4 | 2015 | 5.5" | 12.93 square inches (4.8" × 2.7") | 2560 × 1440 QHD | 16:09 | 534.04 | 41.9 |
| Samsung Galaxy S7 Edge | 2016 | 5.5" | 12.93 square inches (4.8" × 2.7") | 2560 × 1440 QHD | 16:09 | 534.04 | 41.9 |
| Motorola Mobility Moto Z | 2016 | 5.5" | 12.93 square inches (4.8" × 2.7") | 2560 × 1440 QHD | 16:09 | 534.04 | 41.9 |
| Google Pixel XL | 2016 | 5.5" | 12.93 square inches (4.8" × 2.7") | 2560 × 1440 QHD | 16:09 | 534.04 | 41.9 |
| Motorola Moto Z2 Force | 2017 | 5.5" | 12.93 square inches (4.8" × 2.7") | 2560 × 1440 QHD | 16:09 | 534.04 | 41.9 |
| Samsung Galaxy S10+ | 2019 | 6.3" | 15.36 square inches (5.7" × 2.7") | 3040 × 1440 | 19:09 | 533.94 | 45 |
| Samsung Galaxy S8+ | 2017 | 6.2" | 15.12 square inches (5.6" × 2.7") | 2960 × 1440 | 37:18:00 | 530.92 | 44.5 |
| Samsung Galaxy S9+ | 2018 | 6.2" | 15.12 square inches (5.6" × 2.7") | 2960 × 1440 | 37:18:00 | 530.92 | 44.5 |
| Samsung Galaxy Note 8 | 2017 | 6.3" | 15.61 square inches (5.7" × 2.8") | 2960 × 1440 | 37:18:00 | 522.49 | 44 |
| Google Pixel 3 XL | 2018 | 6.3" | 15.61 square inches (5.7" × 2.8") | 2960 × 1440 | 37:18:00 | 522.49 | 44 |
| Samsung Galaxy Note 4 | 2014 | 5.7" | 13.88 square inches (5" × 2.8") | 2560 × 1440 QHD | 16:09 | 515.3 | 42.3 |

-continued

| Manufacturer and model name | Year introduced | Screen size | Screen area | Resolution | Ratio | PPI | PPD |
|---|---|---|---|---|---|---|---|
| Samsung Galaxy Note 5 | 2015 | 5.7" | 13.88 square inches (5" × 2.8") | 2560 × 1440 QHD | 16:09 | 515.3 | 42.3 |
| Motorola Moto X Style | 2015 | 5.7" | 13.88 square inches (5" × 2.8") | 2560 × 1440 QHD | 16:09 | 515.3 | 42.3 |
| Huawei Nexus 6P | 2015 | 5.7" | 13.88 square inches (5" × 2.8") | 2560 × 1440 QHD | 16:09 | 515.3 | 42.3 |
| Samsung Galaxy Note 7 | 2016 | 5.7" | 13.88 square inches (5" × 2.8") | 2560 × 1440 QHD | 16:09 | 515.3 | 42.3 |
| LG V20 | 2016 | 5.7" | 13.88 square inches (5" × 2.8") | 2560 × 1440 QHD | 16:09 | 515.3 | 42.3 |
| Samsung Galaxy Note 9 | 2018 | 6.4" | 16.11 square inches (5.8" × 2.8") | 2960 × 1440 | 37:18:00 | 514.33 | 43.4 |
| Essential PH-1 | 2017 | 5.71" | 13.23 square inches | 2560 × 1312 | 80:41:00 | 503.79 | 41.5 |
| Samsung Galaxy S10 5G | 2019 | 6.7" | 17.37 square inches (6.1" × 2.9") | 3040 × 1440 | 19:09 | 502.06 | 42.9 |
| Samsung Note10+ | 2019 | 6.8" | 17.89 square inches (6.1" × 2.9") | 3040 × 1440 | 19:09 | 494.68 | 42.4 |
| Motorola Nexus 6 | 2014 | 5.96" | 15.18 square inches (5.2" × 2.9") | 2560 × 1440 QHD | 16:09 | 492.82 | 40.7 |
| Sharp SH-02F | 2014 | 4.5" | 8.65 square inches (3.9" × 2.2") | 1920 × 1080 FHD | 16:09 | 489.53 | 38.8 |
| Vivo Xplay 3S | 2014 | 6" | 15.38 square inches (5.2" × 2.9") | 2560 × 1440 QHD | 16:09 | 489.53 | 40.5 |
| Lenovo Vibe Z2 Pro | 2014 | 6" | 15.38 square inches (5.2" × 2.9") | 2560 × 1440 QHD | 16:09 | 489.53 | 40.5 |
| HTC One | 2013 | 4.7" | 9.44 square inches (2.3" × 4.1") | 1080 × 1920 | 9:16 | 468.7 | 35.6 |
| Apple iPhone X | 2017 | 5.8" | 12.8 square inches (5.3" × 2.4") | 2436 × 1125 | 812:375 | 462.63 | 38.3 |
| Apple iPhone XS | 2018 | 5.8" | 12.8 square inches (5.3" × 2.4") | 2436 × 1125 | 812:375 | 462.63 | 38.3 |
| Apple iPhone 11 Pro | 2019 | 5.8" | 12.8 square inches (5.3" × 2.4") | 2436 × 1125 | 812:375 | 462.63 | 38.3 |
| Sharp SH-06E | 2013 | 4.8" | 9.84 square inches (4.2" × 2.4") | 1920 × 1080 FHD | 16:09 | 458.94 | 36.6 |
| Apple iPhone XS Max | 2018 | 6.5" | 16.09 square inches (5.9" × 2.7") | 2688 × 1242 | 448:207 | 455.55 | 38.7 |
| Apple iPhone 11 Pro Max | 2019 | 6.5" | 16.09 square inches (5.9" × 2.7") | 2688 × 1242 | 448:207 | 455.55 | 38.7 |
| BlackBerry Passport | 2014 | 4.5" | 10.13 square inches (3.2" × 3.2") | 1440 × 1440 | 1:01 | 452.55 | 35.1 |
| Google Nexus 5 | 2013 | 4.95" | 10.47 square inches (4.3" × 2.4") | 1920 × 1080 FHD | 16:09 | 445.03 | 35.7 |
| TCL Palm | 2018 | 3.3" | 4.65 square inches (2.9" × 1.6") | 1280 × 720 WXGA-H | 16:09 | 445.03 | 34.2 |
| Google Pixel 3a | 2019 | 5.6" | 12.34 square inches (5" × 2.4") | 2220 × 1080 | 37:18:00 | 440.85 | 35.4 |
| HTC J Butterfly | 2012 | 5" | 10.68 square inches (2.5" × 4.4") | 1080 × 1920 | 9:16 | 440.58 | 35.4 |
| Samsung Galaxy S4 | 2013 | 5" | 10.68 square inches (4.4" × 2.5") | 1920 × 1080 FHD | 16:09 | 440.58 | 35.4 |
| Sony Xperia Z | 2013 | 5" | 10.68 square inches (2.5" × 4.4") | 1080 × 1920 | 9:16 | 440.58 | 35.4 |
| Huawei Ascend D2 | 2013 | 5" | 10.68 square inches (2.5" × 4.4") | 1080 × 1920 | 9:16 | 440.58 | 35.4 |
| Nokia Lumia 929 | 2014 | 5.0" | 10.68 square inches (4.4" × 2.5") | 1920 × 1080 FHD | 16:09 | 440.58 | 35.4 |
| Nokia Lumia 930 | 2014 | 5" | 10.68 square inches (4.4" × 2.5") | 1920 × 1080 FHD | 16:09 | 440.58 | 35.4 |
| Sony Xperia Z1 | 2013 | 5" | 10.68 square inches (4.4" × 2.5") | 1920 × 1080 FHD | 16:09 | 440.58 | 35.4 |
| HTC Butterfly S | 2013 | 5" | 10.68 square inches (4.4" × 2.5") | 1920 × 1080 FHD | 16:09 | 440.58 | 35.4 |
| HTC One A9 | 2015 | 5" | 10.68 square inches (4.4" × 2.5") | 1920 × 1080 FHD | 16:09 | 440.58 | 35.4 |
| Google Pixel | 2016 | 5" | 10.68 square inches (4.4" × 2.5") | 1920 × 1080 FHD | 16:09 | 440.58 | 35.4 |
| Google Pixel 2 | 2017 | 5" | 10.68 square inches (4.4" × 2.5") | 1920 × 1080 FHD | 16:09 | 440.58 | 35.4 |
| Google Pixel 3 | 2018 | 5.5" | 12.1 square inches | 2160 × 1080 | 2:01 | 439.08 | 35.9 |
| LG Q6 Alpha | 2017 | 5.5" | 12.1 square inches (4.9" × 2.5") | 2160 × 1080 | 2:01 | 439.08 | 35.9 |
| Samsung Galaxy S10e | 2019 | 5.8" | 13.01 square inches (5.2" × 2.5") | 2280 × 1080 | 19:09 | 434.98 | 36 |

Numerous modifications and variations of the present disclosure are possible in light of the above teachings. It is therefore to be understood that within the scope of the appended claims, the disclosure may be practised otherwise than as specifically described herein.

We claim:

1. An eye examination apparatus for use with at least one smartphone, comprising:
   a body having a first eye opening and a second eye opening for a user to see into the eye examination apparatus using two eyes;
   a first coupling for receiving a first portable electronic device having a display and a camera and for holding the first portable electronic device in a predefined position in relation to the body, such that the camera of the first portable electronic device is positioned to acquire ophthalmic images through the first eye opening via line of sight, and the display of the first portable electronic device is viewable through the second eye opening via line of sight;
   a semi-transparent mirror or prism coupled to the body; and
   a second coupling for receiving a second portable electronic device having a display and a camera and for holding the second portable electronic device in a predefined position in relation to the body, such that the camera of the second portable electronic device is positioned to acquire ophthalmic images through the second eye opening via reflection off of the semitransparent mirror or prism, and the display of the second portable electronic device is viewable through the first eye opening via reflection off of the semi-transparent mirror or prism;
   wherein the semi-transparent mirror or prism is positioned to enable the reflections for the second portable electronic device but is transparent enough to enable the line of sight for the camera and the display of the first portable electronic device through the semi-transparent mirror or prism.

2. The eye examination apparatus of claim 1, wherein the first coupling and the second coupling are configured to hold the first portable electronic device and the second portable electronic device orthogonally to one another, and the semi-transparent mirror or prism is a semitransparent mirror oriented at 45-degree angle relative to the first portable electronic device and the second portable electronic device to facilitate the reflections for the second portable electronic device.

3. The eye examination apparatus of claim 2, wherein the second coupling is configured to hold the second portable electronic device on a top portion of the body.

4. The eye examination apparatus of claim 2, wherein the second coupling is configured to hold the second smartphone on a bottom portion of the body.

5. The eye examination apparatus of claim 1, wherein:
   the first coupling comprises a first cartridge that holds the first portable electronic device, such that the first cartridge is slidably insertable into the body; and
   the second coupling comprises a second cartridge that holds the second portable electronic device, such that the second cartridge is slidably insertable into the body.

6. The eye examination apparatus of claim 1, further comprising:
   a first eye lens for the first eye opening and a second eye lens for the second eye opening.

7. The eye examination apparatus of claim 6, wherein the first eye lens is laterally movable within the first eye opening and the second eye lens is laterally movable within the second eye opening, the eye examination apparatus further comprising an interpupillary distance adjustment mechanism for adjusting an amount of separation between the optical axes of the first eye lens and the second eye lens.

8. The eye examination apparatus of claim 7, wherein the interpupillary distance adjustment mechanism comprises a vertically moveable guide member defining angled channels that engage the first eye lens and the second eye lens and are shaped such that downward movement of the guide member moves the first the first eye lens and the second eye lens closer together and upward movement of the guide member moves the first the first eye lens and the second eye lens farther apart, and an actuator on a top portion of the body for moving the guide member.

9. The eye examination apparatus of claim 7, wherein the interpupillary distance adjustment mechanism comprises:
   a rack gear extending inwardly from a frame of each of the first eye lens and the second eye lens,
   a pinion gear mounted in the body between the first eye lens and the second eye lens and engaged by the rack gears such that movement of one of the first eye lens and the second eye lens towards the pinion gear also causes movement of the other of the first eye lens and the second eye lens; and
   an adjustment knob extending laterally outwardly from the body and coupled to a worm gear within a post extending laterally from the frame of one of the first eye lens and the second eye lens.

10. The eye examination apparatus of claim 7, wherein the interpupillary distance adjustment mechanism comprises a lever mounted on the body and pivotally coupled to a frame of one of the first eye lens and the second eye lens.

11. The eye examination apparatus of claim 1, further comprising:
   at least one light emitter positioned to generate infrared or visible light out of the first eye opening and the second eye opening via reflection off of the semi-transparent mirror or prism.

12. The eye examination apparatus of claim 11, wherein the at least one light emitter comprises a first infrared emitter positioned to generate infrared light out of the first eye opening and a second infrared emitter positioned to generate infrared light out of the second eye opening.

13. The eye examination apparatus of claim 1, further comprising at least one condenser lens configured to render a divergent beam from a light emitter of the second portable electronic device into a converging beam for funduscopy involving image capturing by the camera of the first portable electronic device.

14. The eye examination apparatus of claim 1, further comprising at least one condenser lens configured to render a divergent beam from a light emitter of the first portable electronic device into a converging beam for funduscopy involving image capturing by the camera of the second portable electronic device.

15. The eye examination apparatus of claim 1, further comprising:
   components for interferometry including a low coherence light source and a mirror; and
   wherein the low coherence light source is positioned facing the mirror through the semi-transparent mirror or prism, such that low coherence light from the low coherence light source can be split by the semi-transparent mirror or prism into a reference light wave through the semitransparent mirror or prism and a sample light wave reflected off of the semi-transparent mirror or prism; wherein the reference light reflects off of the mirror, reflects off of the semi-transparent mirror or prism, and is received by the camera of the first portable electronic device; wherein the sample light wave light reflects off of a sample, passes through the semi-transparent mirror or prism, and is received by the camera of the first portable electronic device; wherein the camera of the first portable electronic device is positioned to detect interference between the reference light wave and the sample light wave.

16. The eye examination apparatus of claim 15, wherein the components for interferometry further comprises a 2D MEMS (Microelectromechanical) mirror for beam steering the sample wave and a lens to condense the sample wave into a converging beam at the sample.

17. The eye examination apparatus of claim 1, further comprising refraction apparatus for refraction eye examination.

18. The eye examination apparatus of claim 1, further comprising at least one occluder.

19. The eye examination apparatus of claim 18, wherein the at least one occlude comprises a pair of occluders each having a plurality of pinholes configured to eliminate disorganized refracted light arrays which cause blurred vision in non-neurological eye conditions.

20. The eye examination apparatus of claim 1, wherein the first eye opening and the second eye opening are separate openings.

*    *    *    *    *